(12) United States Patent
Truckai et al.

(10) Patent No.: US 9,421,059 B2
(45) Date of Patent: *Aug. 23, 2016

(54) DEVICE FOR ENDOMETRIAL ABLATION HAVING AN EXPANDABLE SEAL FOR A CERVICAL CANAL

(75) Inventors: Daniel C. Truckai, Saratoga, CA (US); Csaba Truckai, Saratoga, CA (US)

(73) Assignee: Minerva Surgical, Inc., Cupertino, CA (US)

( * ) Notice: Subject to any disclaimer, the term of this patent is extended or adjusted under 35 U.S.C. 154(b) by 201 days.

This patent is subject to a terminal disclaimer.

(21) Appl. No.: 13/094,715

(22) Filed: Apr. 26, 2011

(65) Prior Publication Data

US 2012/0101332 A1 Apr. 26, 2012

Related U.S. Application Data

(60) Provisional application No. 61/328,533, filed on Apr. 27, 2010.

(51) Int. Cl.
*A61M 29/00* (2006.01)
*A61B 18/04* (2006.01)
(Continued)

(52) U.S. Cl.
CPC ......... *A61B 18/042* (2013.01); *A61B 18/1485* (2013.01); *A61B 2018/0022* (2013.01); *A61B 2018/00166* (2013.01); *A61B 2018/00285* (2013.01); *A61B 2018/00559* (2013.01); *A61B 2018/00577* (2013.01); *A61B 2018/00642* (2013.01); *A61B 2018/00702* (2013.01); *A61B 2018/00791* (2013.01); *A61B 2018/00827* (2013.01); *A61B 2018/00863* (2013.01); *A61B 2018/00875* (2013.01); *A61B 2018/00892* (2013.01)

(58) Field of Classification Search
CPC ............ A61B 18/1485; A61B 18/042; A61B 2018/00285; A61B 2018/00166; A61B 2018/0022; A61B 2018/00559; A61B 2017/4225; A61B 2018/00892; A61B 17/12136; A61B 2018/00863; A61M 2210/1433
USPC .......................... 606/191–199, 33, 34, 41, 27
See application file for complete search history.

(56) References Cited

U.S. PATENT DOCUMENTS

| 3,227,154 A | 1/1966 | Cook |
| 3,247,841 A | 4/1966 | Cook |
| 3,313,291 A | 4/1967 | Cook |

(Continued)

FOREIGN PATENT DOCUMENTS

WO  WO 2008022479 A1 * 2/2008

OTHER PUBLICATIONS

Kurman, edited by Robert J. (1994). Blaustein's Pathology of the Female Genital Tract (4th ed.). New York, NY: Springer New York. pp. 185-201. ISBN 978-1-4757-3889-6.*

(Continued)

*Primary Examiner* — Katrina Stransky
(74) *Attorney, Agent, or Firm* — Wilson Sonsini Goodrich & Rosati

(57) ABSTRACT

Methods, systems and devices for endometrial ablation. In accordance with a method, a working end of an RF ablation device is positioned in a patient uterus to contact endometrial tissue, the working end comprising a dielectric wall capable of non-expanded and expanded shapes and for conforming to an asymmetric or symmetric shape of the patient's cervix. An expandable seal is provided for sealing the cervical canal.

6 Claims, 24 Drawing Sheets

(51) Int. Cl.
*A61B 18/14* (2006.01)
*A61B 18/00* (2006.01)

(56) References Cited

U.S. PATENT DOCUMENTS

| | | | |
|---|---|---|---|
| 3,385,300 A | 5/1968 | Holter | |
| 4,089,337 A | 5/1978 | Kronner | |
| 4,198,981 A * | 4/1980 | Sinnreich | 606/193 |
| 4,325,387 A | 4/1982 | Helfer | |
| 4,349,033 A | 9/1982 | Eden | |
| 4,430,076 A | 2/1984 | Harris | |
| 4,611,604 A | 9/1986 | Botvidsson et al. | |
| 4,944,307 A | 7/1990 | Hon et al. | |
| 4,966,161 A | 10/1990 | Wallace et al. | |
| 4,979,948 A | 12/1990 | Geddes et al. | |
| 5,098,375 A | 3/1992 | Baier | |
| 5,184,619 A | 2/1993 | Austin | |
| 5,191,883 A | 3/1993 | Lennox et al. | |
| 5,433,216 A | 7/1995 | Sugrue et al. | |
| 5,439,441 A | 8/1995 | Grimsley et al. | |
| 5,540,658 A * | 7/1996 | Evans et al. | 604/101.04 |
| 5,542,928 A * | 8/1996 | Evans et al. | 604/113 |
| 5,549,546 A | 8/1996 | Schneider et al. | |
| 5,566,680 A | 10/1996 | Urion et al. | |
| 5,653,692 A | 8/1997 | Masterson et al. | |
| 5,733,230 A | 3/1998 | Sawchuck et al. | |
| 5,769,880 A | 6/1998 | Truckai et al. | |
| 5,787,892 A | 8/1998 | Dabney | |
| 5,891,094 A | 4/1999 | Masterson et al. | |
| 5,891,134 A | 4/1999 | Goble et al. | |
| 5,925,038 A | 7/1999 | Panescu et al. | |
| 5,935,098 A | 8/1999 | Blaisdell et al. | |
| 5,951,497 A | 9/1999 | Wallace et al. | |
| 5,984,879 A | 11/1999 | Wallace et al. | |
| 6,041,260 A | 3/2000 | Stern et al. | |
| 6,057,689 A | 5/2000 | Saadat | |
| 6,066,132 A * | 5/2000 | Chen et al. | 606/28 |
| 6,080,118 A | 6/2000 | Blythe | |
| 6,231,524 B1 | 5/2001 | Wallace et al. | |
| 6,296,639 B1 | 10/2001 | Truckai et al. | |
| 6,319,208 B1 | 11/2001 | Abita et al. | |
| 6,485,410 B1 * | 11/2002 | Loy | 600/135 |
| 6,554,780 B1 | 4/2003 | Sampson et al. | |
| 6,625,495 B1 | 9/2003 | Alon et al. | |
| 6,635,054 B2 * | 10/2003 | Fjield et al. | 606/27 |
| 6,663,626 B2 | 12/2003 | Truckai et al. | |
| 6,712,815 B2 | 3/2004 | Sampson et al. | |
| 6,736,811 B2 | 5/2004 | Panescu et al. | |
| 6,740,047 B2 | 5/2004 | Holmes et al. | |
| 6,743,184 B2 | 6/2004 | Sampson et al. | |
| 6,813,520 B2 | 11/2004 | Truckai et al. | |
| 6,872,183 B2 | 3/2005 | Sampson et al. | |
| 7,063,670 B2 | 6/2006 | Sampson et al. | |
| 7,105,007 B2 | 9/2006 | Hibler | |
| 7,112,177 B2 | 9/2006 | Christensen et al. | |
| 7,147,606 B1 | 12/2006 | Chang et al. | |
| 7,198,602 B2 | 4/2007 | Eide | |
| 7,335,162 B2 | 2/2008 | Eide | |
| 7,371,231 B2 | 5/2008 | Rioux et al. | |
| 7,381,190 B2 | 6/2008 | Sugrue et al. | |
| 7,462,157 B2 | 12/2008 | Jarrell | |
| 7,479,120 B2 | 1/2009 | Gregersen | |
| 7,512,445 B2 | 3/2009 | Truckai et al. | |
| 7,577,476 B2 | 8/2009 | Hochman et al. | |
| 7,585,280 B2 | 9/2009 | Wilson et al. | |
| 7,775,985 B2 | 8/2010 | Eide | |
| 7,892,181 B2 | 2/2011 | Christensen et al. | |
| 2002/0161304 A1 | 10/2002 | Eide | |
| 2004/0122463 A1 * | 6/2004 | Hibler | 606/191 |
| 2005/0107665 A1 | 5/2005 | Nady | |
| 2005/0107721 A1 | 5/2005 | Whalen et al. | |
| 2005/0143728 A1 | 6/2005 | Sampson et al. | |
| 2005/0177130 A1 * | 8/2005 | Konstantino et al. | 604/509 |
| 2005/0240211 A1 | 10/2005 | Sporri et al. | |
| 2005/0283092 A1 | 12/2005 | Gedebou | |
| 2005/0288603 A1 | 12/2005 | Goping | |
| 2006/0047240 A1 | 3/2006 | Kumar et al. | |
| 2006/0052666 A1 | 3/2006 | Kumar et al. | |
| 2006/0073728 A1 | 4/2006 | Zaiken et al. | |
| 2006/0122556 A1 | 6/2006 | Kumar et al. | |
| 2006/0122557 A1 | 6/2006 | Kumar et al. | |
| 2006/0212043 A1 | 9/2006 | Grillo | |
| 2007/0021713 A1 | 1/2007 | Kumar et al. | |
| 2007/0032814 A1 * | 2/2007 | Hibler | 606/193 |
| 2007/0060834 A1 | 3/2007 | Odland et al. | |
| 2007/0066990 A1 * | 3/2007 | Marsella et al. | 606/193 |
| 2007/0142750 A1 | 6/2007 | Kotmel et al. | |
| 2007/0255167 A1 | 11/2007 | Christensen et al. | |
| 2007/0288051 A1 * | 12/2007 | Beyer et al. | 606/193 |
| 2008/0004566 A1 | 1/2008 | Sloan | |
| 2008/0027358 A1 | 1/2008 | Gregersen et al. | |
| 2008/0077053 A1 | 3/2008 | Epstein et al. | |
| 2008/0097425 A1 | 4/2008 | Truckai | |
| 2008/0103408 A1 | 5/2008 | Denton et al. | |
| 2008/0119868 A1 * | 5/2008 | Sharp et al. | 606/119 |
| 2008/0167664 A1 | 7/2008 | Payne et al. | |
| 2008/0194996 A1 | 8/2008 | Kassab | |
| 2008/0287833 A1 | 11/2008 | Semler et al. | |
| 2008/0319339 A1 | 12/2008 | Beute | |
| 2009/0054892 A1 | 2/2009 | Rioux et al. | |
| 2009/0062688 A1 | 3/2009 | Eide | |
| 2009/0062689 A1 | 3/2009 | Eide | |
| 2009/0069711 A1 | 3/2009 | Eide | |
| 2009/0082698 A1 | 3/2009 | Kassab | |
| 2009/0125014 A1 | 5/2009 | Bouthillier et al. | |
| 2009/0163908 A1 | 6/2009 | MacLean et al. | |
| 2009/0270759 A1 | 10/2009 | Wilson et al. | |
| 2010/0100091 A1 | 4/2010 | Truckai | |
| 2010/0100094 A1 | 4/2010 | Truckai | |
| 2010/0198214 A1 | 8/2010 | Layton et al. | |
| 2010/0210941 A1 | 8/2010 | Kim et al. | |
| 2010/0222708 A1 | 9/2010 | Hitchcock et al. | |
| 2010/0256623 A1 | 10/2010 | Nicolas | |
| 2010/1030555 | 12/2010 | Chu | |

OTHER PUBLICATIONS

Third party observations dated Sep. 6, 2013 for EP Application No. 10830743.0.

* cited by examiner

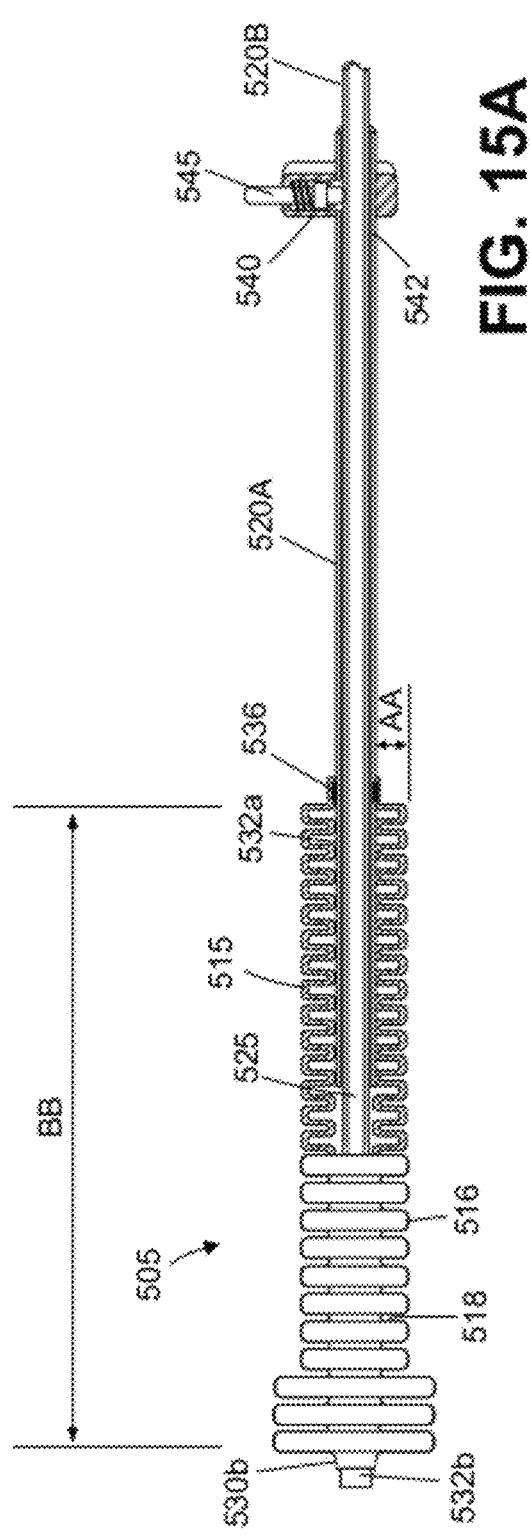
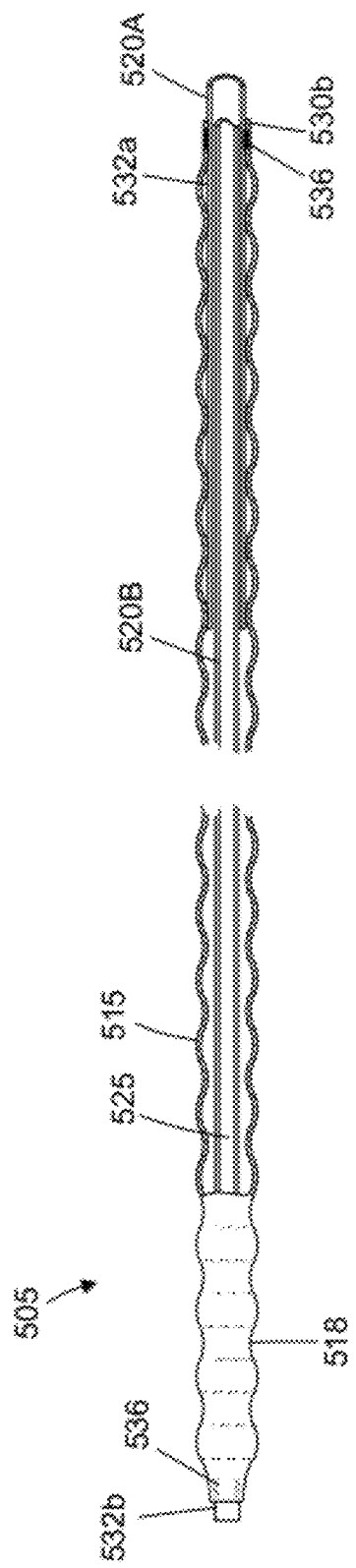
FIG. 15A
FIG. 15B

DEVICE FOR ENDOMETRIAL ABLATION HAVING AN EXPANDABLE SEAL FOR A CERVICAL CANAL

CROSS-REFERENCES TO RELATED APPLICATIONS

This application claims the benefit of U.S. Provisional Application No. 61/328,533, filed Apr. 27, 2010, the full disclosure of which is incorporated herein by reference.

BACKGROUND

1. Field of the Invention

The present invention relates to electrosurgical methods and devices for global endometrial ablation in a treatment of menorrhagia. More particularly, the present invention relates to applying radiofrequency current to endometrial tissue by means of capacitively coupling the current through an expandable, thin-wall dielectric member enclosing an ionized gas.

A variety of devices have been developed or proposed for endometrial ablation. Of relevance to the present invention, a variety of radiofrequency ablation devices have been proposed including solid electrodes, balloon electrodes, metalized fabric electrodes, and the like. While often effective, many of the prior electrode designs have suffered from one or more deficiencies, such as relatively slow treatment times, incomplete treatments, non-uniform ablation depths, and risk of injury to adjacent organs.

For these reasons, it would be desirable to provide systems and methods that allow for endometrial ablation using radiofrequency current which is rapid, provides for controlled ablation depth and which reduce the risk of injury to adjacent organs. At least some of these objectives will be met by the invention described herein.

2. Description of the Background Art

U.S. Pat. Nos. 5,769,880; 6,296,639; 6,663,626; and 6,813,520 describe intrauterine ablation devices formed from a permeable mesh defining electrodes for the application of radiofrequency energy to ablate uterine tissue. U.S. Pat. No. 4,979,948 describes a balloon filled with an electrolyte solution for applying radiofrequency current to a mucosal layer via capacitive coupling. US 2008/097425, having common inventorship with the present application, describes delivering a pressurized flow of a liquid medium which carries a radiofrequency current to tissue, where the liquid is ignited into a plasma as it passes through flow orifices. U.S. Pat. No. 5,891,134 describes a radiofrequency heater within an enclosed balloon. U.S. Pat. No. 6,041,260 describes radiofrequency electrodes distributed over the exterior surface of a balloon which is inflated in a body cavity to be treated. U.S. Pat. No. 7,371,231 and US 2009/054892 describe a conductive balloon having an exterior surface which acts as an electrode for performing endometrial ablation. U.S. Pat. No. 5,191,883 describes bipolar heating of a medium within a balloon for thermal ablation. U.S. Pat. Nos. 6,736,811 and 5,925,038 show an inflatable conductive electrode.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention provides methods, systems and devices for evaluating the integrity of a uterine cavity. The uterine cavity may be perforated or otherwise damaged by the transcervical introduction of probes and instruments into the uterine cavity. If the uterine wall is perforated, it would be preferable to defer any ablation treatment until the uterine wall is healed. A method of the invention comprises introducing transcervically a probe into a patient's uterine cavity, providing a flow of a fluid (e.g., $CO_2$) through the probe into the uterine cavity and monitoring the rate of the flow to characterize the uterine cavity as perforated or non-perforated based on a change in the flow rate. If the flow rate drops to zero or close to zero, this indicates that the uterine cavity is intact and not perforated. If the flow rate does not drop to zero or close to zero, this indicates that a fluid flow is leaking through a perforation in the uterine cavity into the uterine cavity or escaping around an sealing structure that occludes the cervical canal.

Embodiments herein provide a system for treating uterine tissue, comprising an expandable RF energy delivery surface for positioning in a uterine cavity; an RF source configured to deliver current across the surface; and a sealing structure disposed adjacent the energy delivery surface and configured for positioning in and sealing a cervical canal.

The sealing structure may be, for example, an elongated bellows-like member with a compliant wall. In embodiments, the sealing structure has a longitudinal axis, and has a repose state with a plurality of annular ridges for engaging tissue surrounding a cervical canal. The sealing structure can be axially stretched to provide a reduced cross section for insertion in the patient's uterine canal.

In further embodiments, the sealing structure is elongated with a distal portion having a greater cross section in a repose state, and a proximal portion with a lesser cross section in a repose state.

The sealing structure may be carried concentrically around a distal portion of a sleeve assembly or support member that carries the RF energy delivery surface of the endometrial ablation system.

In embodiments, the energy delivery surface comprises a wall surrounding an interior chamber. The wall may include at least partly a dielectric. The wall may further include an electrode. The interior chamber may be fluid-tight.

In accordance with still further embodiments, a method of treating uterine tissue is provided, comprising expanding a RF energy delivery surface within a patient's uterine cavity; expanding an expandable member in the patient's cervical canal; and activating an RF source configured to deliver current across the surface to ablate endometrial tissue.

In further embodiments, expanding the RF energy delivery surface comprises expanding a frame supporting the surface.

For a fuller understanding of the nature and advantages of the present invention, reference should be made to the ensuing detailed description and accompanying drawings.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 15A is a cut-away view of the cervical seal of FIG. 14 in a repose shape.

FIG. 15B is a cut-away view of the cervical seal of FIGS. 14 and 15A in a stretched, tensioned shape.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

In general, an electrosurgical ablation system is described herein that comprises an elongated introducer member for accessing a patient's uterine cavity with a working end that deploys an expandable thin-wall dielectric structure containing an electrically non-conductive gas as a dielectric. In one embodiment, an interior chamber of the thin-wall dielectric structure contains a circulating neutral gas such as argon. An RF power source provides current that is coupled to the neutral gas flow by a first polarity electrode disposed within the interior chamber and a second polarity electrode at an exterior of the working end. The gas flow, which is converted to a conductive plasma by an electrode arrangement, functions as a switching mechanism that permits current flow to engaged endometrial tissue only when the voltage across the combination of the gas, the thin-wall dielectric structure and the engaged tissue reaches a threshold that causes capacitive coupling across the thin-wall dielectric material. By capacitively coupling current to tissue in this manner, the system provides a substantially uniform tissue effect within all tissue in contact with the expanded dielectric structure. Further, the invention allows the neutral gas to be created contemporaneously with the capacitive coupling of current to tissue.

In general, this disclosure may use the terms "plasma," "conductive gas" and "ionized gas" interchangeably. A plasma consists of a state of matter in which electrons in a neutral gas are stripped or "ionized" from their molecules or atoms. Such plasmas can be formed by application of an electric field or by high temperatures. In a neutral gas, electrical conductivity is non-existent or very low. Neutral gases act as a dielectric or insulator until the electric field reaches a breakdown value, freeing the electrons from the atoms in an avalanche process thus forming a plasma. Such a plasma provides mobile electrons and positive ions, and acts as a conductor which supports electric currents and can form spark or arc. Due to their lower mass, the electrons in a plasma accelerate more quickly in response to an electric field than the heavier positive ions, and hence carry the bulk of the current.

Figure 1:
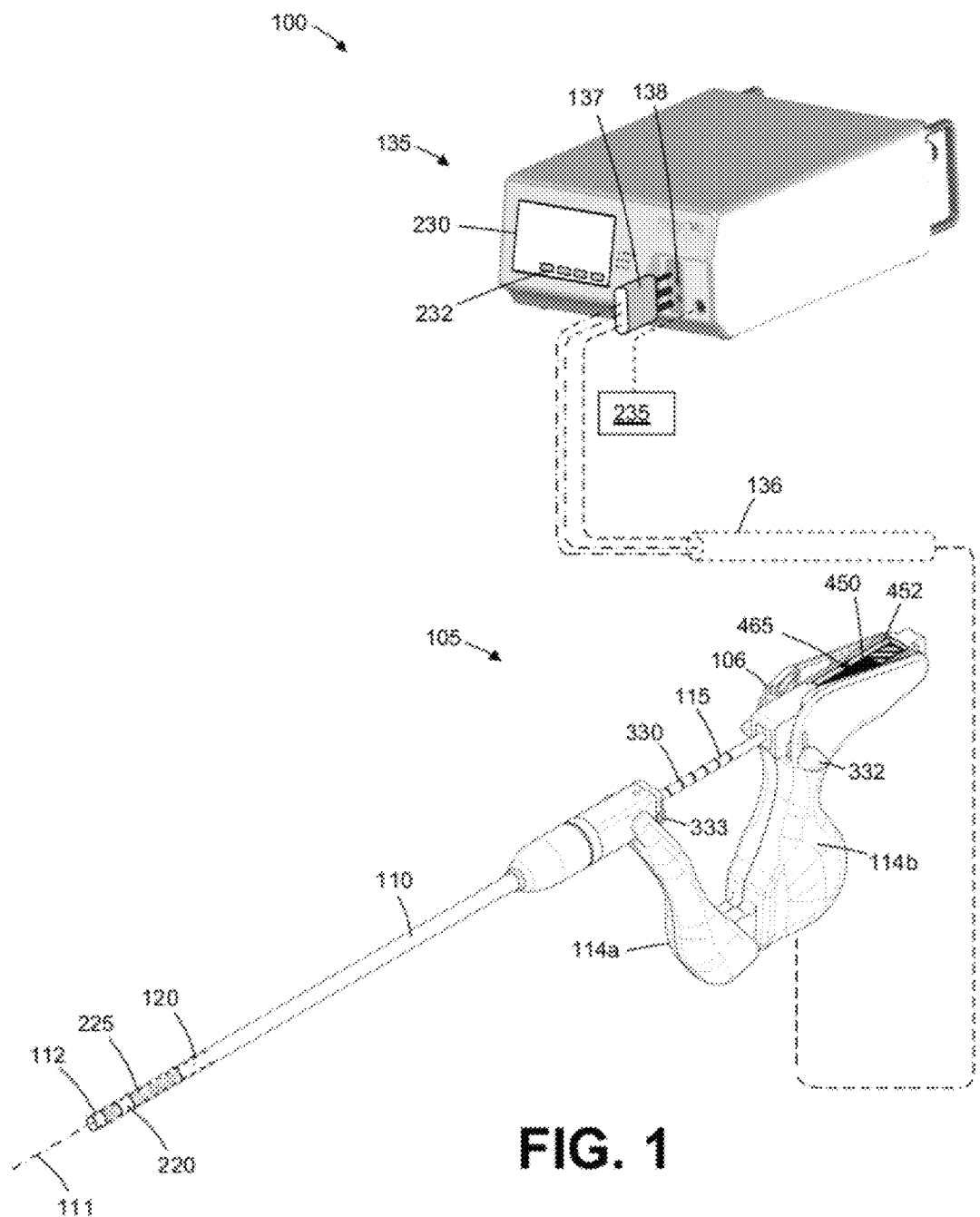
FIG. 1 is a perspective view of an ablation system corresponding to the invention, including a hand-held electrosurgical device for endometrial ablation, RF power source, gas source and controller.
Figure 2:
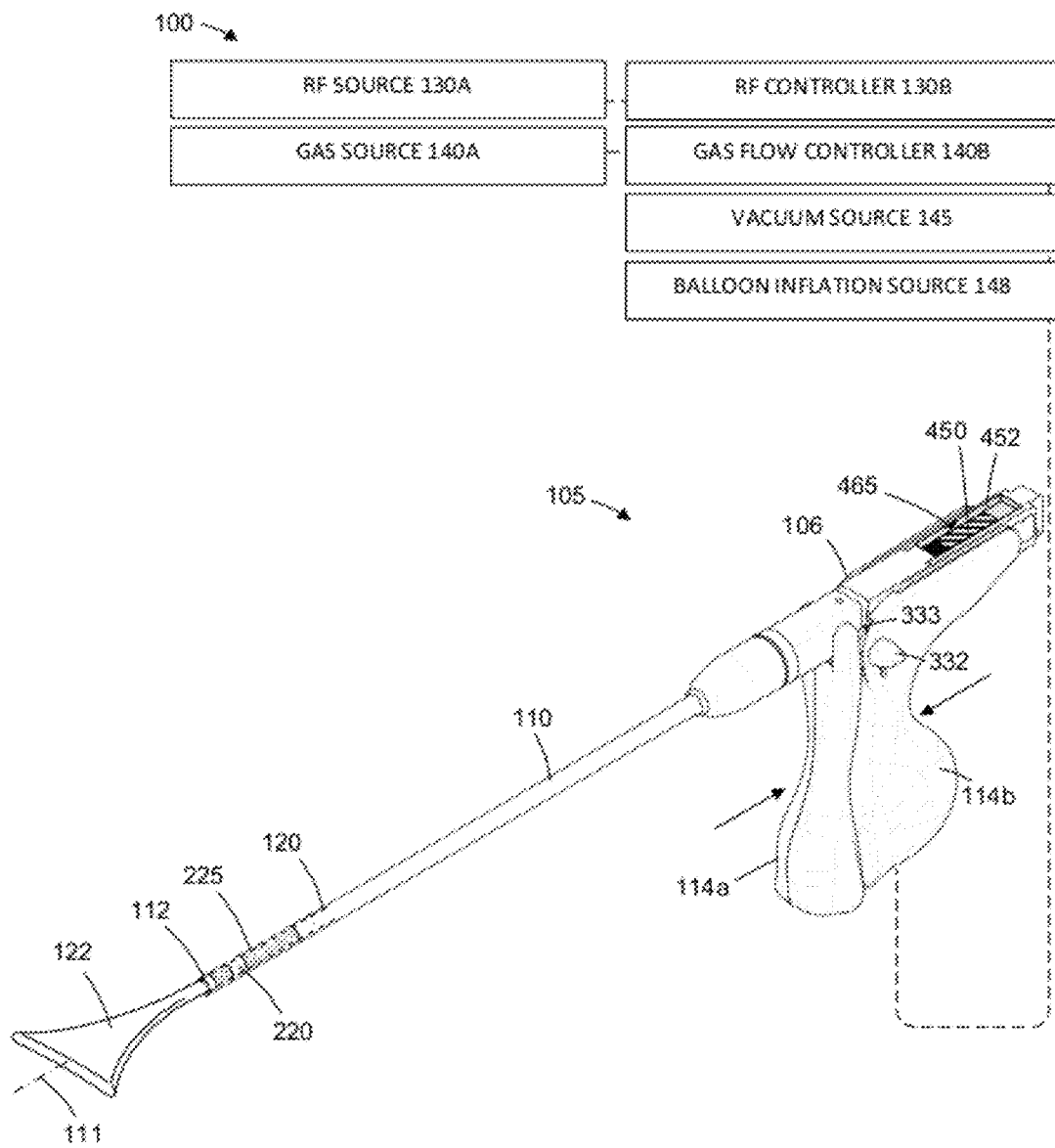
FIG. 2 is a view of the hand-held electrosurgical device of FIG. 1 with a deployed, expanded thin-wall dielectric structure.

FIG. 1 depicts one embodiment of an electrosurgical ablation system 100 configured for endometrial ablation. The system 100 includes a hand-held apparatus 105 with a proximal handle 106 shaped for grasping with a human hand that is coupled to an elongated introducer sleeve 110 having axis 111 that extends to a distal end 112. The introducer sleeve 110 can be fabricated of a thin-wall plastic, composite, ceramic or metal in a round or oval cross-section having a diameter or major axis ranging from about 4 mm to 8 mm in at least a distal portion of the sleeve that accesses the uterine cavity. The handle 106 is fabricated of an electrically insulative material such as a molded plastic with a pistol-grip having first and second portions, 114a and 114b, that can be squeezed toward one another to translate an elongated translatable sleeve 115 which is housed in a bore 120 in the elongated introducer sleeve 110. By actuating the first and second handle portions, 114a and 114b, a working end 122 can be deployed from a first retracted position (FIG. 1) in the distal portion of bore 120 in introducer sleeve 110 to an extended position as shown in FIG. 2. In FIG. 2, it can be seen that the first and second handle portions, 114a and 114b, are in a second actuated position with the working end 122 deployed from the bore 120 in introducer sleeve 110.

Figure 3:
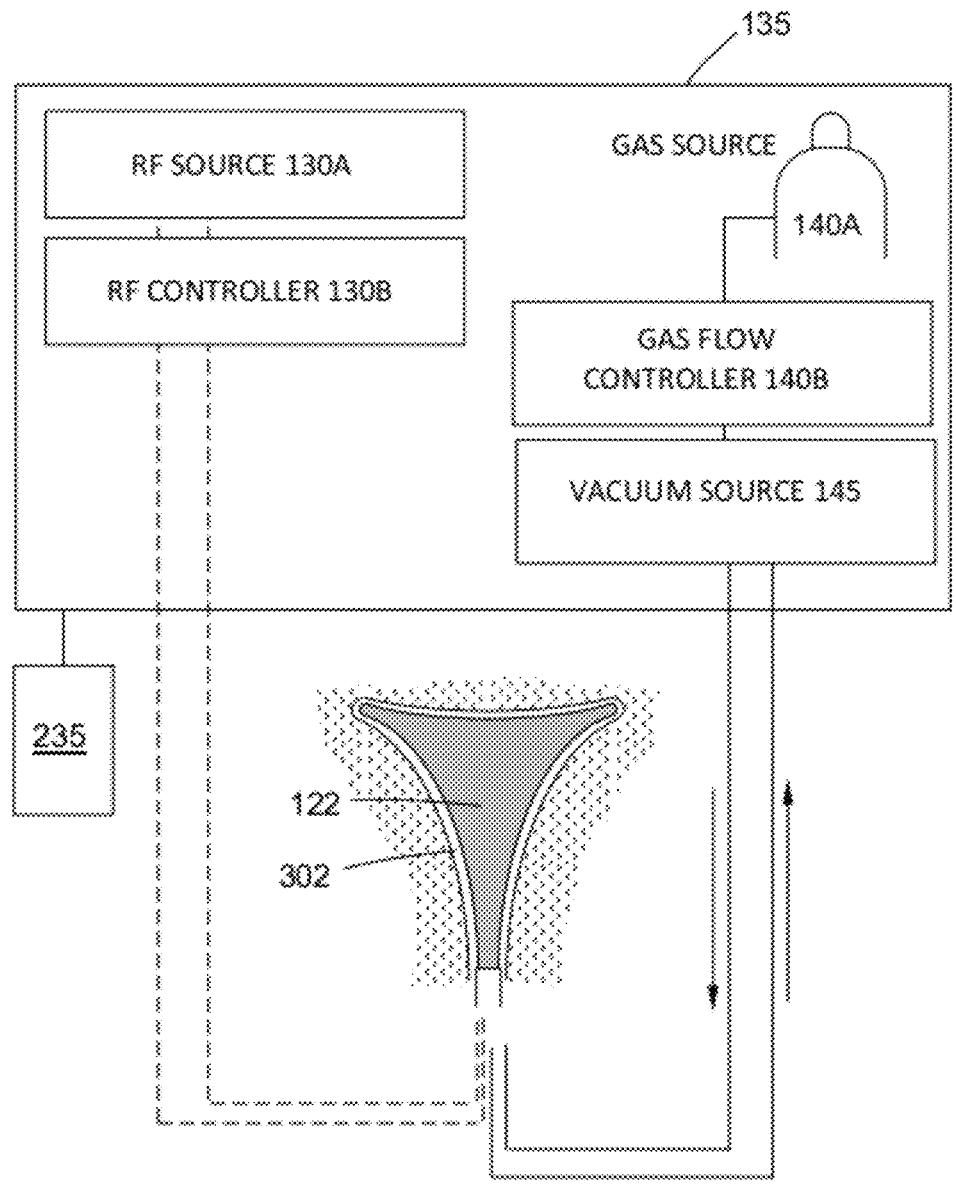
FIG. 3 is a block diagram of components of one electrosurgical system corresponding to the invention.

FIGS. 2 and 3 shows that ablation system 100 includes an RF energy source 130A and RF controller 130B in a control unit 135. The RF energy source 130A is connected to the hand-held device 105 by a flexible conduit 136 with a plug-in connector 137 configured with a gas inflow channel, a gas outflow channel, and first and second electrical leads for connecting to receiving connector 138 in the control unit 135. The control unit 135, as will be described further below in FIGS. 3 and 4, further comprises a neutral gas inflow source 140A, gas flow controller 140B and optional vacuum or negative pressure source 145 to provide controlled gas inflows and gas outflows to and from the working end 122. The control unit 135 further includes a balloon inflation source 148 for inflating an expandable sealing balloon 225 carried on introducer sleeve 110 as described further below.

Referring to FIG. 2, the working end 122 includes a flexible, thin-wall member or structure 150 of a dielectric material that when expanded has a triangular shape configured for contacting the patient's endometrial lining that is targeted for ablation. In one embodiment as shown in FIGS. 2, 5 and 6, the dielectric structure 150 comprises a thin-wall material such as silicone with a fluid-tight interior chamber 152.

In an embodiment, an expandable-collapsible frame assembly 155 is disposed in the interior chamber. Alternatively, the dielectric structure may be expanded by a neutral gas without a frame, but using a frame offers a number of advantages. First, the uterine cavity is flattened with the opposing walls in contact with one another. Expanding a balloon-type member may cause undesirable pain or spasms. For this reason, a flat structure that is expanded by a frame is better suited for deployment in the uterine cavity. Second, in embodiments herein, the neutral gas is converted to a conductive plasma at a very low pressure controlled by gas inflows and gas outflows—so that any pressurization of a balloon-type member with the neutral gas may exceed a desired pressure range and would require complex controls of gas inflows and gas outflows. Third, as described below, the frame provides an electrode for contact with the neutral gas in the interior chamber 152 of the dielectric structure 150, and the frame 155 extends into all regions of the interior chamber to insure electrode exposure to all regions of the neutral gas and plasma. The frame 155 can be constructed of any flexible material with at least portions of the frame functioning as spring elements to move the thin-wall structure 150 from a collapsed configuration (FIG. 1) to an expanded, deployed configuration (FIG. 2) in a patient's uterine cavity. In one embodiment, the frame 155 comprises stainless steel elements 158a, 158b and 160a and 160b that function akin to leaf springs. The frame can be a stainless steel such as 316 SS, 17A SS, 420 SS, 440 SS or the frame can be a NiTi material. The frame preferably extends along a single plane, yet remains thin transverse to the plane, so that the frame may expand into the uterine cavity. The frame elements can have a thickness ranging from about 0.005" to 0.025". As can be seen in FIGS. 5 and 6, the proximal ends 162a and 162b of spring elements 158a, 158b are fixed (e.g., by welds 164) to the distal end 165 of sleeve member 115. The proximal ends 166a and 166b of spring elements 160a, 160b are welded to distal portion 168 of a secondary translatable sleeve 170 that can be extended from bore 175 in translatable sleeve 115. The secondary translatable sleeve 170 is dimensioned for a loose fit in bore 175 to allow gas flows within bore 175. FIGS. 5 and 6 further illustrate the distal ends 176a and 176b of spring elements 158a, 158b are welded to distal ends 178a and 178b of spring elements 160a and 160b to thus provide a frame 155 that can be moved from a linear shape (see FIG. 1) to an expanded triangular shape (FIGS. 5 and 6).

As will be described further below, the bore 175 in sleeve 115 and bore 180 in secondary translatable sleeve 170 function as gas outflow and gas inflow lumens, respectively. It should be appreciated that the gas inflow lumen can comprise any single lumen or plurality of lumens in either sleeve 115 or sleeve 170 or another sleeve, or other parts of the frame 155 or the at least one gas flow lumen can be formed into a wall of dielectric structure 150. In FIGS. 5, 6 and 7 it can be seen that gas inflows are provided through bore 180 in sleeve 170, and gas outflows are provided in bore 175 of sleeve 115. However, the inflows and outflows can be also be reversed between bores 175 and 180 of the various sleeves. FIGS. 5 and 6 further show that a rounded bumper element 185 is provided at the distal end of sleeve 170 to insure that no sharp edges of the distal end of sleeve 170 can contact the inside of the thin dielectric wall 150. In one embodiment, the bumper element 185 is silicone, but it could also comprise a rounded metal element. FIGS. 5 and 6 also show that a plurality of gas inflow ports 188 can be provided along a length of in sleeve 170 in chamber 152, as well as a port 190 in the distal end of sleeve 170 and bumper element 185. The sectional view of FIG. 7 also shows the gas flow passageways within the interior of introducer sleeve 110.

Figure 5:
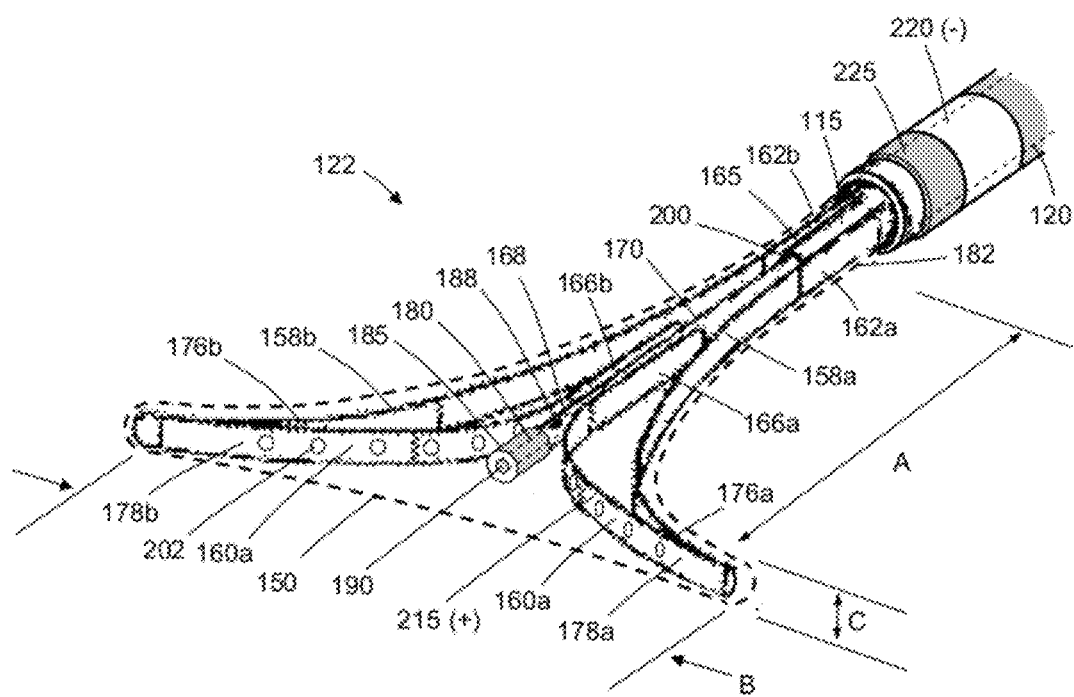
FIG. 5 is an enlarged perspective view of the expanded thin-wall dielectric structure, showing an expandable-collapsible frame with the thin dielectric wall in phantom view.
Figure 6:
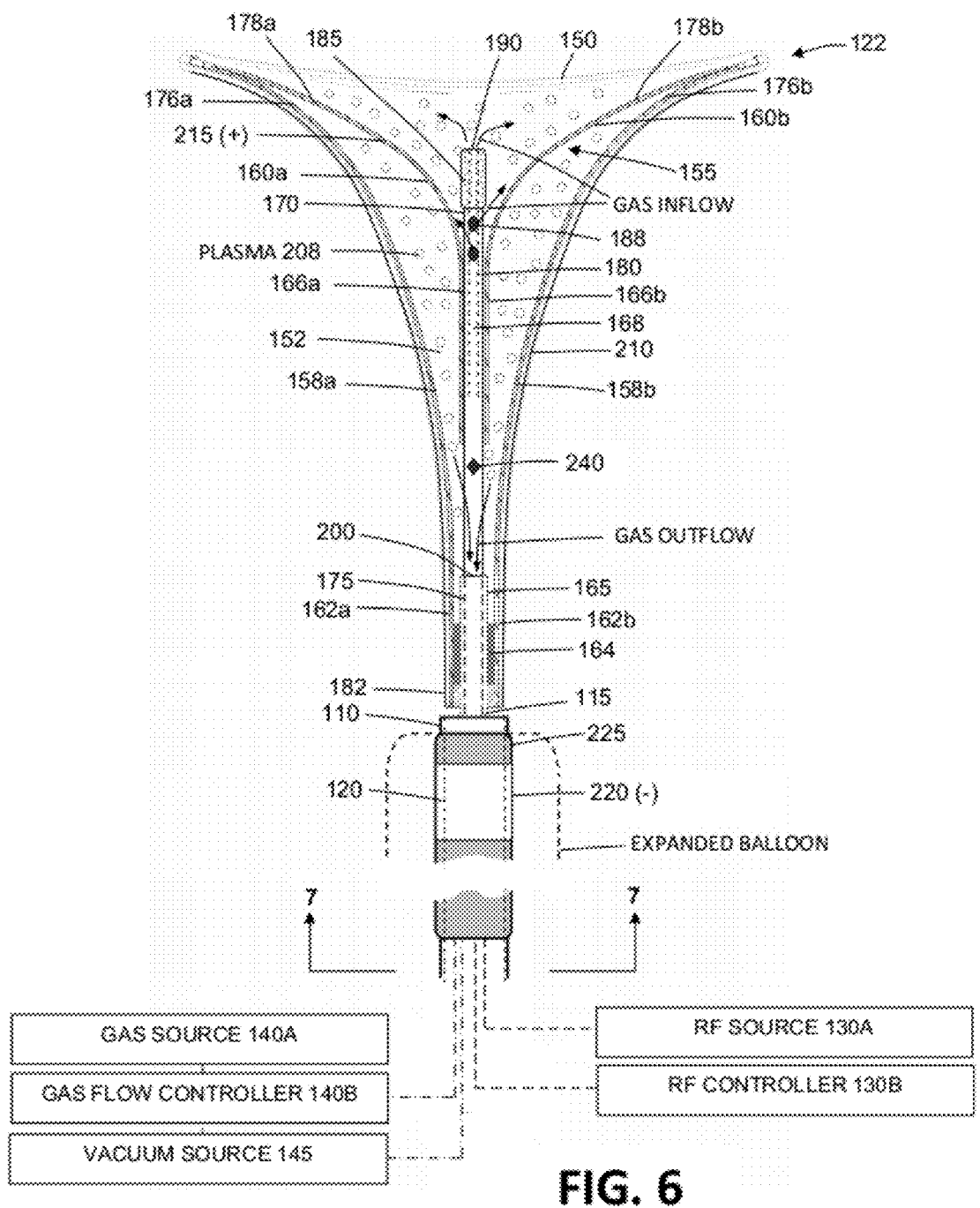
FIG. 6 is a partial sectional view of the expanded thin-wall dielectric structure of FIG. 5 showing (i) translatable members of the expandable-collapsible frame a that move the structure between collapsed and (ii) gas inflow and outflow lumens.
Figure 7:
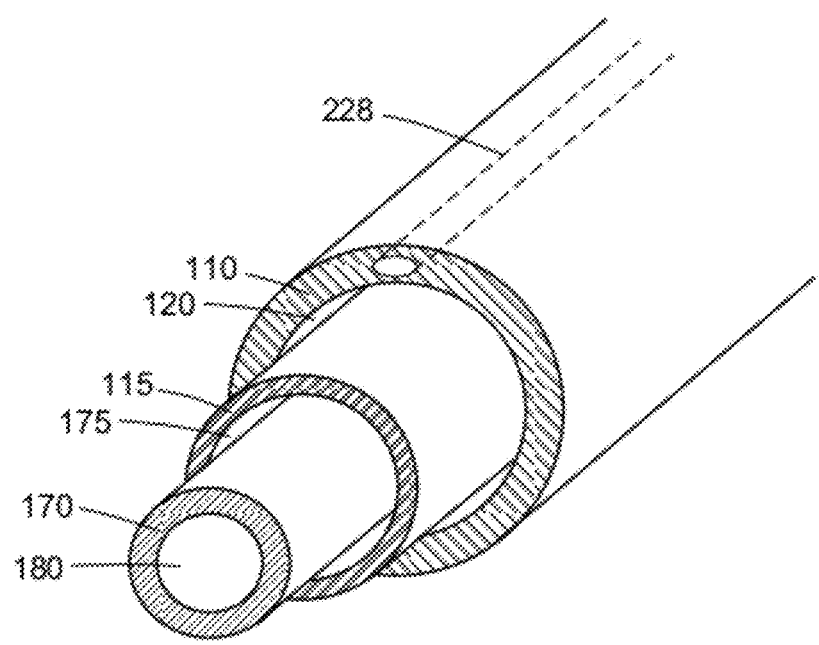
FIG. 7 is a sectional view of an introducer sleeve showing various lumens of the introducer sleeve taken along line 7-7 of FIG. 6.

It can be understood from FIGS. 1, 2, 5 and 6 that actuation of first and second handle portions, 114a and 114b, (i) initially causes movement of the assembly of sleeves 115 and 170 relative to bore 120 of introducer sleeve 110, and (ii) secondarily causes extension of sleeve 170 from bore 175 in sleeve 115 to expand the frame 155 into the triangular shape of FIG. 5. The dimensions of the triangular shape are suited for a patient uterine cavity, and for example can have an axial length A ranging from 4 to 10 cm and a maximum width B at the distal end ranging from about 2 to 5 cm. In one embodiment, the thickness C of the thin-wall structure 150 can be from 1 to 4 mm as determined by the dimensions of spring elements 158a, 158b, 160a and 160b of frame assembly 155. It should be appreciated that the frame assembly 155 can comprise round wire elements, flat spring elements, of any suitable metal or polymer that can provide opening forces to move thin-wall structure 150 from a collapsed configuration to an expanded configuration within the patient uterus. Alternatively, some elements of the frame 155 can be spring elements and some elements can be flexible without inherent spring characteristics.

As will be described below, the working end embodiment of FIGS. 2, 5 and 6 has a thin-wall structure 150 that is formed of a dielectric material such as silicone that permits capacitive coupling of current to engaged tissue while the frame assembly 155 provides structural support to position the thin-wall structure 150 against tissue. Further, gas inflows into the interior chamber 152 of the thin-wall structure can assist in supporting the dielectric wall so as to contact endometrial tissue. The dielectric thin-wall structure 150 can be free from fixation to the frame assembly 155, or can be bonded to an outward-facing portion or portions of frame elements 158a and 158b. The proximal end 182 of thin-wall structure 150 is bonded to the exterior of the distal end of sleeve 115 to thus provide a sealed, fluid-tight interior chamber 152 (FIG. 5).

In one embodiment, the gas inflow source 140A comprises one or more compressed gas cartridges that communicate with flexible conduit 136 through plug-in connector 137 and receiving connector 138 in the control unit 135 (FIGS. 1-2). As can be seen in FIGS. 5-6, the gas inflows from source 140A flow through bore 180 in sleeve 170 to open terminations 188 and 190 therein to flow into interior chamber 152. A vacuum source 145 is connected through conduit 136 and connector 137 to allow circulation of gas flow through the interior chamber 152 of the thin-wall dielectric structure 150. In FIGS. 5 and 6, it can be seen that gas outflows communicate with vacuum source 145 through open end 200 of bore 175 in sleeve 115. Referring to FIG. 5, it can be seen that frame elements 158a and 158b are configured with a plurality of apertures 202 to allow for gas flows through all interior portions of the frame elements, and thus gas inflows from open terminations 188, 190 in bore 180 are free to circulated through interior chamber 152 to return to an outflow path through open end 200 of bore 175 of sleeve 115. As will be described below (see FIGS. 3-4), the gas inflow source 140A is connected to a gas flow or circulation controller 140B which controls a pressure regulator 205 and also controls vacuum source 145 which is adapted for assisting in circulation of the gas. It should be appreciated that the frame elements can be configured with apertures, notched edges or any other configurations that allow for effective circulation of a gas through interior chamber 152 of the thin-wall structure 150 between the inflow and outflow passageways.

Now turning to the electrosurgical aspects of the invention, FIGS. 5 and 6 illustrate opposing polarity electrodes of the system 100 that are configured to convert a flow of neutral gas in chamber 152 into a plasma 208 (FIG. 6) and to allow capacitive coupling of current through a wall 210 of the thin-wall dielectric structure 150 to endometrial tissue in contact with the wall 210. The electrosurgical methods of capacitively coupling RF current across a plasma 208 and dielectric wall 210 are described in U.S. patent application Ser. No. 12/541,043; filed Aug. 13, 2009 and U.S. application Ser. No. 12/541,050, referenced above. In FIGS. 5 and 6, the first polarity electrode 215 is within interior chamber 152 to contact the neutral gas flow and comprises the frame assembly 155 that is fabricated of an electrically conductive stainless steel. In another embodiment, the first polarity electrode can be any element disposed within the interior chamber 152, or extendable into interior chamber 152. The first polarity electrode 215 is electrically coupled to sleeves 115 and 170 which extends through the introducer sleeve 110 to handle 106 and conduit 136 and is connected to a first pole of the RF source energy source 130A and controller 130B. A second polarity electrode 220 is external of the internal chamber 152 and in one embodiment the electrode is spaced apart from wall 210 of the thin-wall dielectric structure 150. In one embodiment as depicted in FIGS. 5 and 6, the second polarity electrode 220 comprises a surface element of an expandable balloon member 225 carried by introducer sleeve 110. The second polarity electrode 220 is coupled by a lead (not shown) that extends through the introducer sleeve 110 and conduit 136 to a second pole of the RF source 130A. It should be appreciated that second polarity electrode 220 can be positioned on sleeve 110 or can be attached to surface portions of the expandable thin-wall dielectric structure 150, as will be described below, to provide suitable contact with body tissue to allow the electrosurgical ablation of the method of the invention. The second polarity electrode 220 can comprise a thin conductive metallic film, thin metal wires, a conductive flexible polymer or a polymeric positive temperature coefficient material. In one embodiment depicted in FIGS. 5 and 6, the expandable member 225 comprises a thin-wall compliant balloon having a length of about 1 cm to 6 cm that can be expanded to seal the cervical canal. The balloon 225 can be inflated with a gas or liquid by any inflation source 148, and can comprise a syringe mechanism controlled manually or by control unit 135. The balloon inflation source 148 is in fluid communication with an inflation lumen 228 in introducer sleeve 110 that extends to an inflation chamber of balloon 225 (see FIG. 7).

Referring back to FIG. 1, the control unit 135 can include a display 230 and touch screen or other controls 232 for setting and controlling operational parameters such as treatment time intervals, treatment algorithms, gas flows, power levels and the like. Suitable gases for use in the system include argon, other noble gases and mixtures thereof. In one embodiment, a footswitch 235 is coupled to the control unit 135 for actuating the system.

Figure 4:
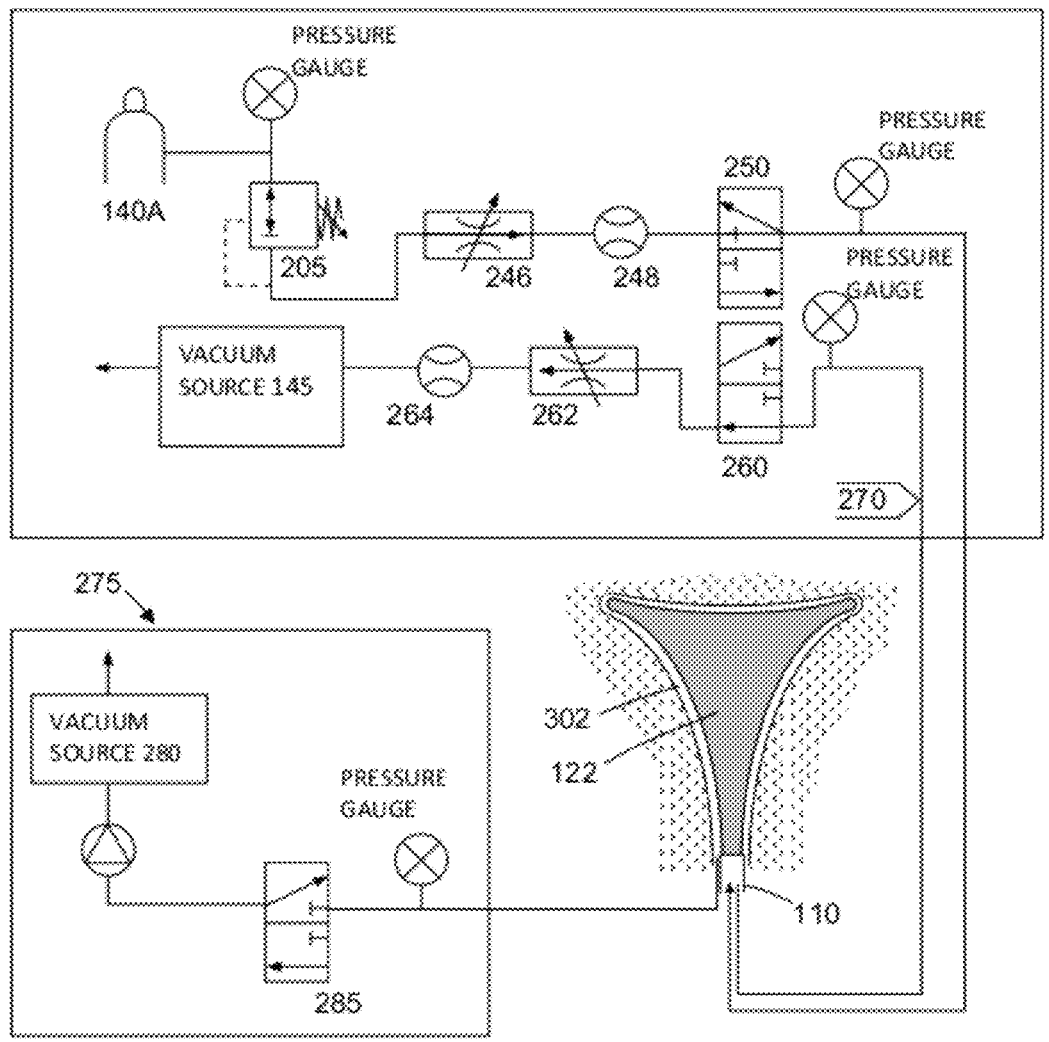
FIG. 4 s a block diagram of the gas flow components of the electrosurgical system of FIG. 1.

The box diagrams of FIGS. 3 and 4 schematically depict the system 100, subsystems and components that are configured for an endometrial ablation system. In the box diagram of FIG. 3, it can be seen that RF energy source 130A and circuitry is controlled by a controller 130B. The system can include feedback control systems that include signals relating to operating parameters of the plasma in interior chamber 152 of the dielectric structure 150. For example, feedback signals can be provided from at least one temperature sensor 240 in the interior chamber 152 of the dielectric structure 150, from a pressure sensor within, or in communication, with interior chamber 152, and/or from a gas flow rate sensor in an inflow or outflow channel of the system. FIG. 4 is a schematic block diagram of the flow control components relating to the flow of gas media through the system 100 and hand-held device 105. It can be seen that a pressurized gas source 140A is linked to a downstream pressure regulator 205, an inflow proportional valve 246, flow meter 248 and normally closed solenoid valve 250. The valve 250 is actuated by the system operator which then allows a flow of a neutral gas from gas source 140A to circulate through flexible conduit 136 and the device 105. The gas outflow side of the system includes a normally open solenoid valve 260, outflow proportional valve 262 and flow meter 264 that communicate with vacuum pump or source 145. The gas can be exhausted into the environment or into a containment system. A temperature sensor 270 (e.g., thermocouple) is shown in FIG. 4 that is configured for monitoring the temperature of outflow gases. FIG. 4 further depicts an optional subsystem 275 which comprises a vacuum source 280 and solenoid valve 285 coupled to the controller 140B for suctioning steam from a uterine cavity 302 at an exterior of the dielectric structure 150 during a treatment interval. As can be understood from FIG. 4, the flow passageway from the uterine cavity 302 can be through bore 120 in sleeve 110 (see FIGS. 2, 6 and 7) or another lumen in a wall of sleeve 110 can be provided.

FIGS. 8A-8D schematically illustrate a method of the invention wherein (i) the thin-wall dielectric structure 150 is deployed within a patient uterus and (ii) RF current is applied to a contained neutral gas volume in the interior chamber 152 to contemporaneously create a plasma 208 in the chamber and capacitively couple current through the thin dielectric wall 210 to apply ablative energy to the endometrial lining to accomplish global endometrial ablation.

Figure 8A:
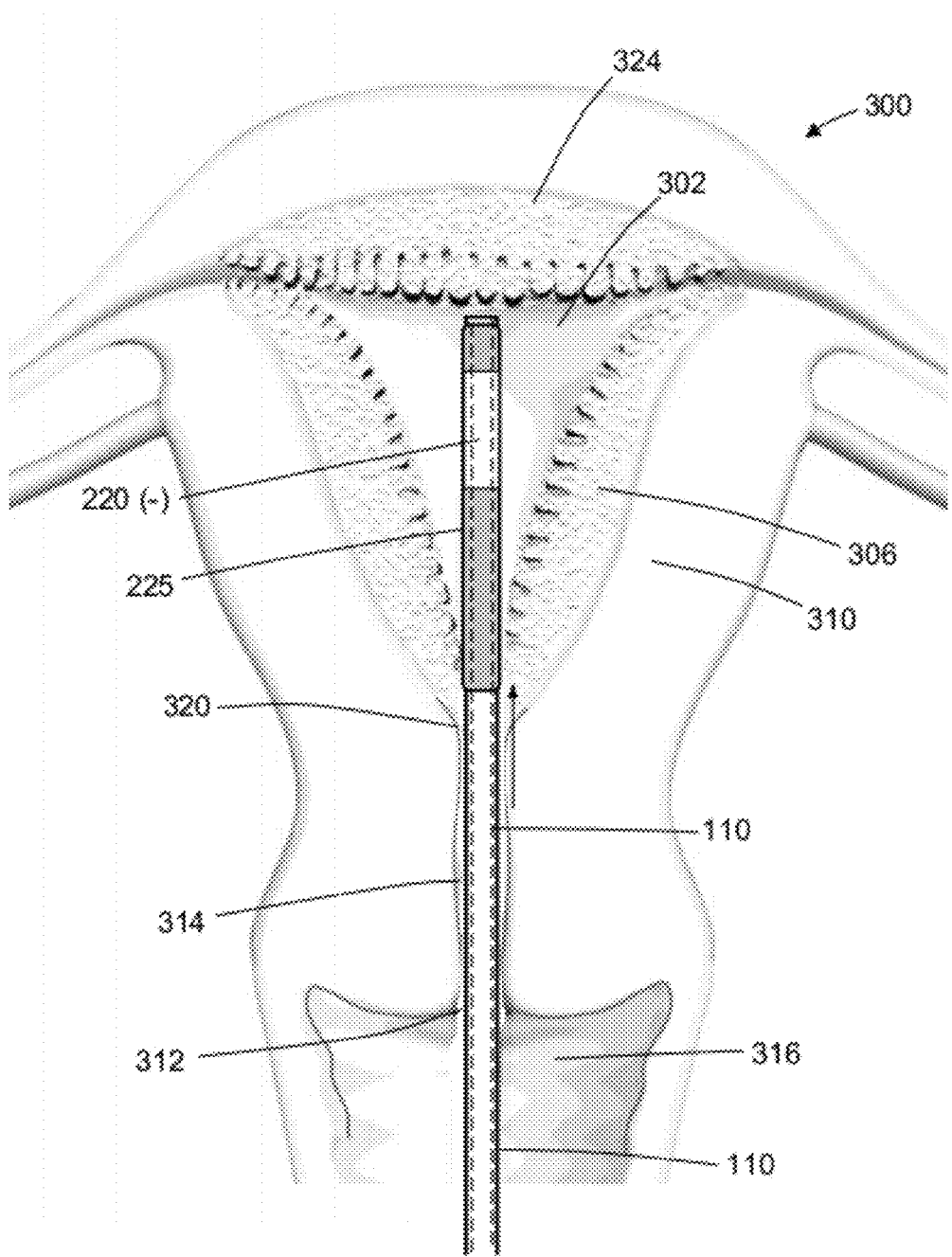
FIG. 8A is an enlarged schematic view of an aspect of a method of the invention illustrating the step introducing an introducer sleeve into a patient's uterus.

More in particular, FIG. 8A illustrates a patient uterus 300 with uterine cavity 302 surrounded by endometrium 306 and myometrium 310. The external cervical os 312 is the opening of the cervix 314 into the vagina 316. The internal os or opening 320 is a region of the cervical canal that opens to the uterine cavity 302. FIG. 8A depicts a first step of a method of the invention wherein the physician has introduced a distal portion of sleeve 110 into the uterine cavity 302. The physician gently can advance the sleeve 110 until its distal tip contacts the fundus 324 of the uterus. Prior to insertion of the device, the physician can optionally introduce a sounding instrument into the uterine cavity to determine uterine dimensions, for example from the internal os 320 to fundus 324.

Figure 8B:
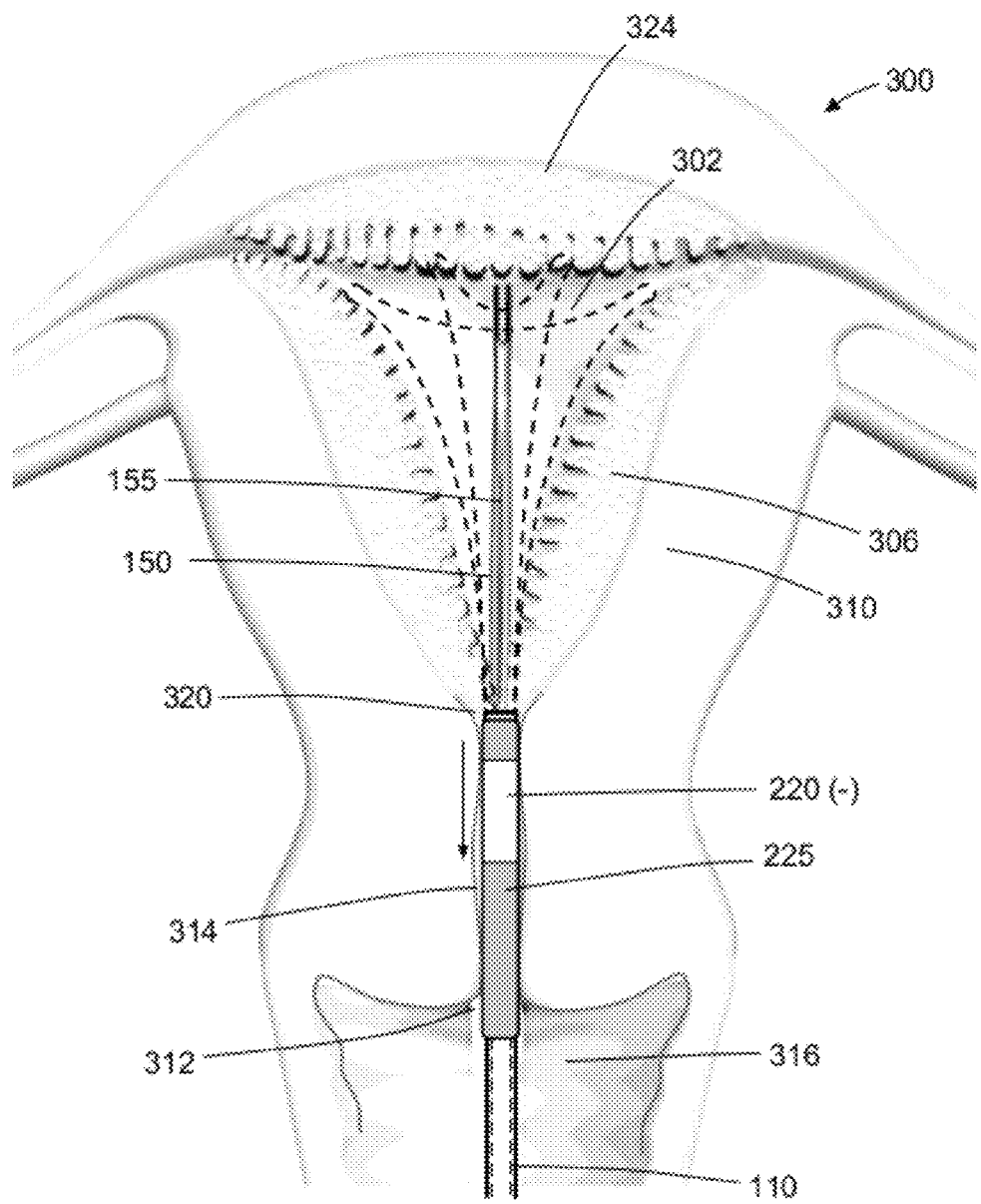
FIG. 8B is a schematic view of a subsequent step of retracting the introducer sleeve to expose a collapsed thin-wall dielectric structure and internal frame in the uterine cavity.

FIG. 8B illustrates a subsequent step of a method of the invention wherein the physician begins to actuate the first and second handle portions, 114a and 114b, and the introducer sleeve 110 retracts in the proximal direction to expose the collapsed frame 155 and thin-wall structure 150 within the uterine cavity 302. The sleeve 110 can be retracted to expose a selected axial length of thin-wall dielectric structure 150, which can be determined by markings 330 on sleeve 115 (see FIG. 1) which indicate the axial travel of sleeve 115 relative to sleeve 170 and thus directly related to the length of deployed thin-wall structure 150. FIG. 2 depicts the handle portions 114a and 114b fully approximated thus deploying the thin-wall structure to its maximum length.

In FIG. 8B, it can be understood that the spring frame elements 158a, 158b, 160a and 160b move the dielectric structure 150 from a non-expanded position to an expanded position in the uterine cavity as depicted by the profiles in dashed lines. The spring force of the frame 155 will expand the dielectric structure 150 until limited by the dimensions of the uterine cavity.

Figure 8C:
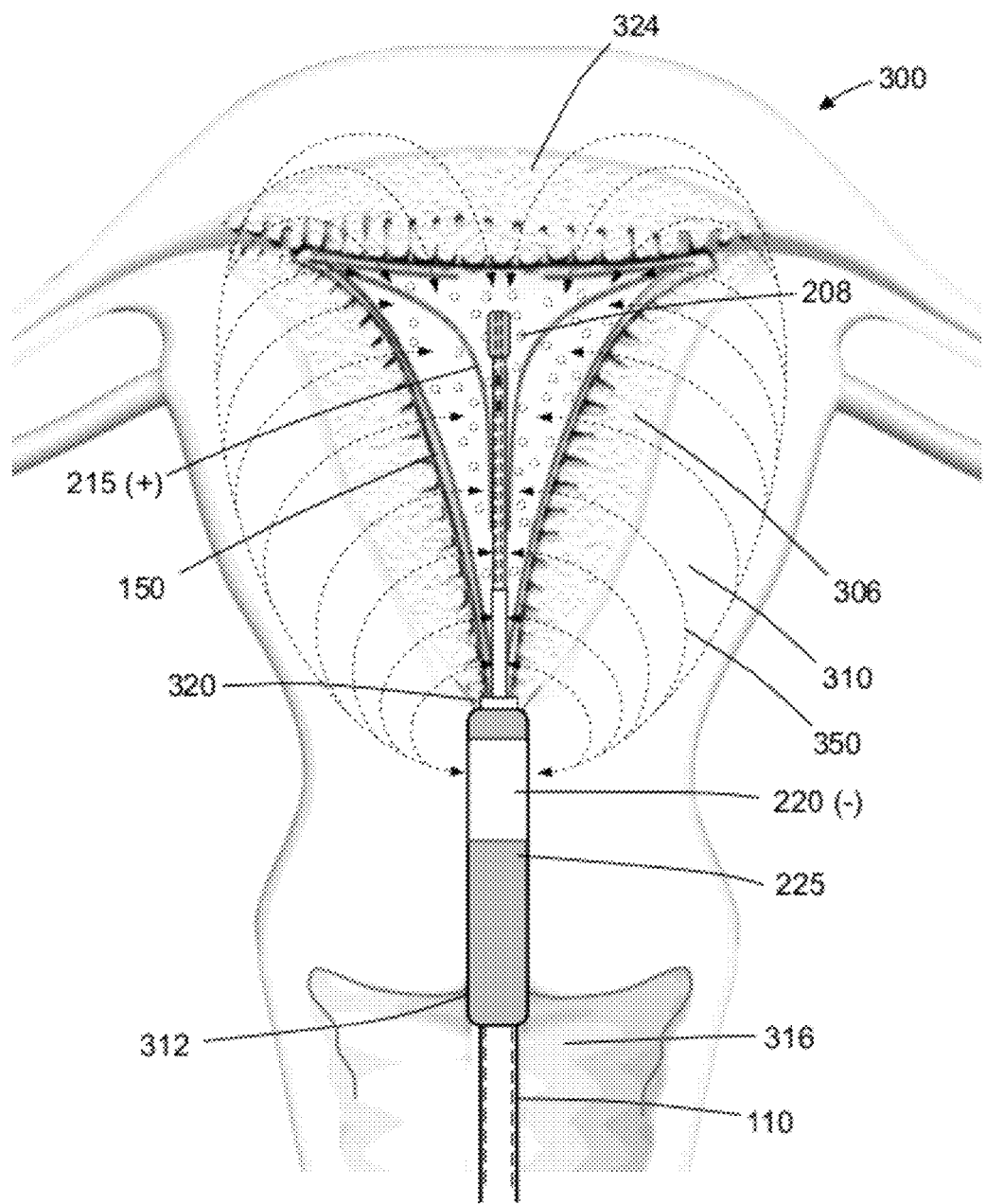
FIG. 8C is a schematic view of subsequent steps of the method, including, (i) actuating the internal frame to move the a collapsed thin-wall dielectric structure to an expanded configuration, (ii) inflating a cervical-sealing balloon carried on the introducer sleeve, and (iii) actuating gas flows and applying RF energy to contemporaneously ionize the gas in the interior chamber and cause capacitive coupling of current through the thin-wall dielectric structure to cause ohmic heating in the engaged tissue indicated by current flow paths.

FIG. 8C illustrates several subsequent steps of a method of the invention. FIG. 8C first depicts the physician continuing to actuate the first and second handle portions, 114a and 114b, which further actuates the frame 155 (see FIGS. 5-6) to expand the frame 155 and thin-wall structure 150 to a deployed triangular shape to contact the patient's endometrial lining 306. The physician can slightly rotate and move the expanding dielectric structure 150 back and forth as the structure is opened to insure it is opened to the desired extent. In performing this step, the physician can actuate handle portions, 114a and 114b, a selected degree which causes a select length of travel of sleeve 170 relative to sleeve 115 which in turn opens the frame 155 to a selected degree. The selected actuation of sleeve 170 relative to sleeve 115 also controls the length of dielectric structure deployed from sleeve 110 into the uterine cavity. Thus, the thin-wall structure 150 can be deployed in the uterine cavity with a selected length, and the spring force of the elements of frame 155 will open the structure 150 to a selected triangular shape to contact or engage the endometrium 306. In one embodiment, the expandable thin-wall structure 150 is urged toward and maintained in an open position by the spring force of elements of the frame 155. In the embodiment depicted in FIGS. 1 and 2, the handle 106 includes a locking mechanism with finger-actuated sliders 332 on either side of the handle that engage a grip-lock element against a notch in housing 333 coupled to introducer sleeve 110 (FIG. 2) to lock sleeves 115 and 170 relative to introducer sleeve 110 to maintain the thin-wall dielectric structure 150 in the selected open position.

FIG. 8C further illustrates the physician expanding the expandable balloon structure 225 from inflation source 148 to thus provide an elongated sealing member to seal the cervix 314 outward from the internal os 320. Following deployment of the thin-wall structure 150 and balloon 225 in the cervix 314, the system 100 is ready for the application of RF energy to ablate endometrial tissue 306. FIG. 8C next depicts the actuation of the system 100, for example, by actuating footswitch 235, which commences a flow of neutral gas from source 140A into the interior chamber 152 of the thin-wall dielectric structure 150. Contemporaneous with, or after a selected delay, the system's actuation delivers RF energy to the electrode arrangement which includes first polarity electrode 215 (+) of frame 155 and the second polarity electrode 220 (−) which is carried on the surface of expandable balloon member 225. The delivery of RF energy delivery will instantly convert the neutral gas in interior chamber 152 into conductive plasma 208 which in turn results in capacitive coupling of current through the dielectric wall 210 of the thin-wall structure 150 resulting in ohmic heating of the engaged tissue. FIG. 8C schematically illustrates the multiplicity of RF current paths 350 between the plasma 208 and the second polarity electrode 220 through the dielectric wall 210. By this method, it has been found that ablation depths of three mm to six mm or more can be accomplished very rapidly, for example in 60 seconds to 120 seconds dependent upon the selected voltage and other operating parameters. In operation, the voltage at which the neutral gas inflow, such as argon, becomes conductive (i.e., converted in part into a plasma) is dependent upon a number of factors controlled by the controllers 130B and 140B, including the pressure of the neutral gas, the volume of interior chamber 152, the flow rate of the gas through the chamber 152, the distance between electrode 210 and interior surfaces of the dielectric wall 210, the dielectric constant of the dielectric wall 210 and the selected voltage applied by the RF source 130, all of which can be optimized by experimentation. In one embodiment, the gas flow rate can be in the range of 5 ml/sec to 50 ml/sec. The dielectric wall 210 can comprise a silicone material having a thickness ranging from a 0.005" to 0.015 and having a relative permittivity in the range of 3 to 4. The gas can be argon supplied in a pressurized cartridge which is commercially available. Pressure in the interior chamber 152 of dielectric structure 150 can be maintained between 14 psia and 15 psia with zero or negative differential pressure between gas inflow source 140A and negative pressure or vacuum source 145. The controller is configured to maintain the pressure in interior chamber in a range that varies by less than 10% or less than 5% from a target pressure. The RF power source 130A can have a frequency of 450 to 550 KHz, and electrical power can be provided within the range of 600 Vrms to about 1200 Vrms and about 0.2 Amps to 0.4 Amps and an effective power of 40 W to 100 W. In one method, the control unit 135 can be programmed to delivery RF energy for a preselected time interval, for example, between 60 seconds and 120 seconds. One aspect of a treatment method corresponding to the invention consists of ablating endometrial tissue with RF energy to elevate endometrial tissue to a temperature greater than 45 degrees Celsius for a time interval sufficient to ablate tissue to a depth of at least 1 mm. Another aspect of the method of endometrial ablation of consists of applying radiofrequency energy to elevate endometrial tissue to a temperature greater than 45 degrees Celsius without damaging the myometrium.

Figure 8D:
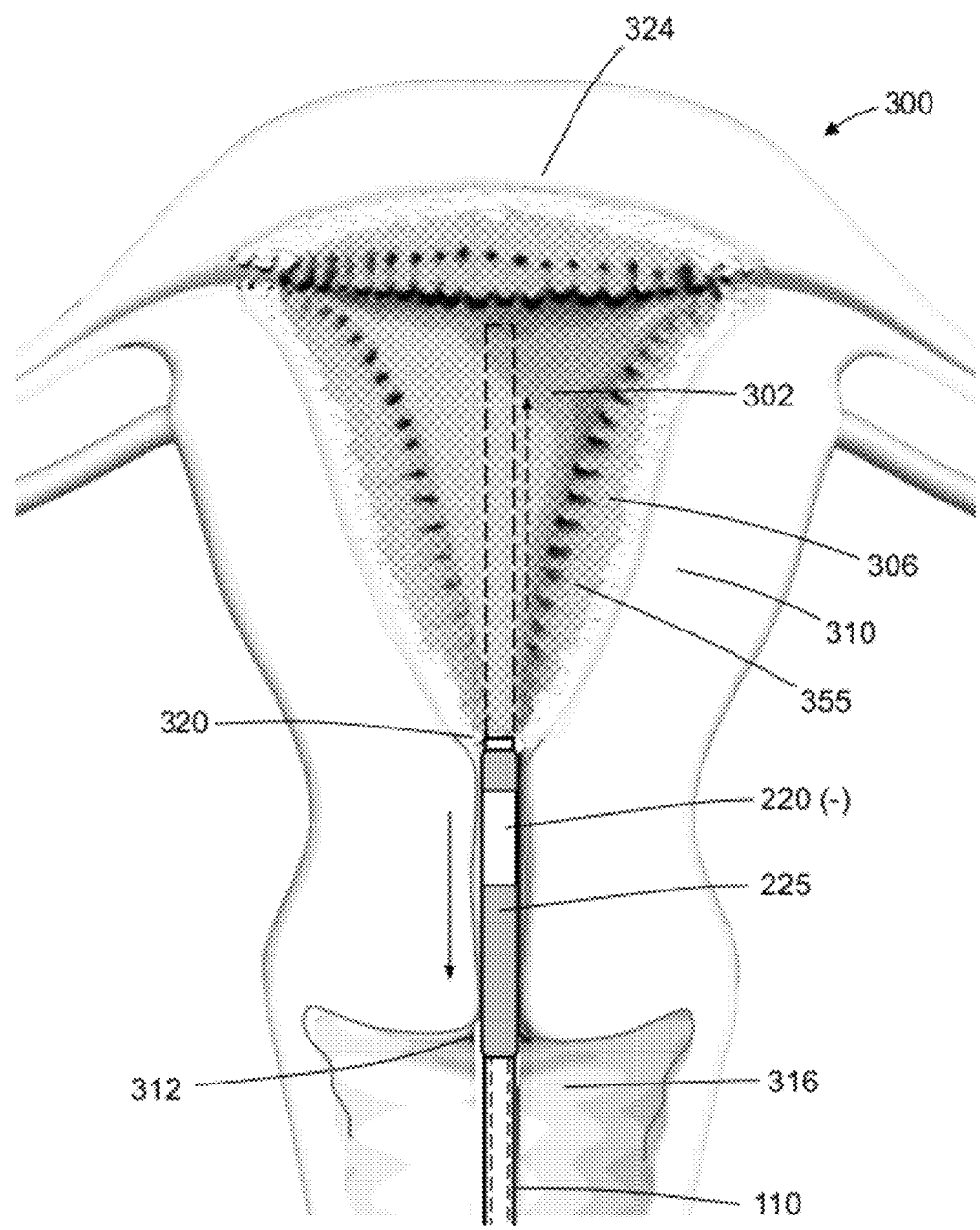
FIG. 8D is a schematic view of a subsequent steps of the method, including: (i) advancing the introducer sleeve over the thin-wall dielectric structure to collapse it into an interior bore shown in phantom view, and (ii) withdrawing the introducer sleeve and dielectric structure from the uterine cavity.

FIG. 8D illustrates a final step of the method wherein the physician deflates the expandable balloon member 225 and then extends sleeve 110 distally by actuating the handles 114a and 114b to collapse frame 155 and then retracting the assembly from the uterine cavity 302. Alternatively, the deployed working end 122 as shown in FIG. 8C can be withdrawn in the proximal direction from the uterine cavity wherein the frame 155 and thin-wall structure 150 will collapse as it is pulled through the cervix. FIG. 8D shows the completed ablation with the ablated endometrial tissue indicated at 360.

In another embodiment, the system can include an electrode arrangement in the handle 106 or within the gas inflow channel to pre-ionize the neutral gas flow before it reaches the interior chamber 152. For example, the gas inflow channel can be configured with axially or radially spaced apart opposing polarity electrodes configured to ionize the gas inflow. Such electrodes would be connected in separate circuitry to an RF source. The first and second electrodes 215 (+) and 220 (−) described above would operate as described above to provide the current that is capacitively coupled to tissue through the walls of the dielectric structure 150. In all other respects, the system and method would function as described above.

Figure 9:
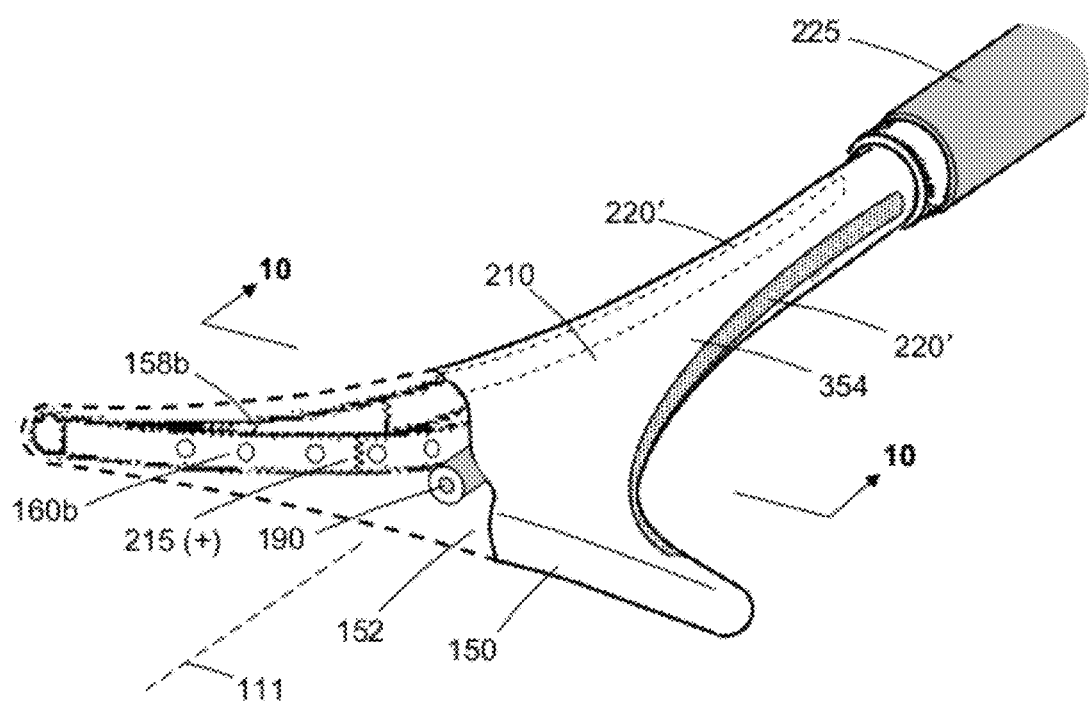
FIG. 9 is a cut-away perspective view of an alternative expanded thin-wall dielectric structure similar to that of FIGS. 5 and 6 show an alternative electrode configuration.
Figure 10:
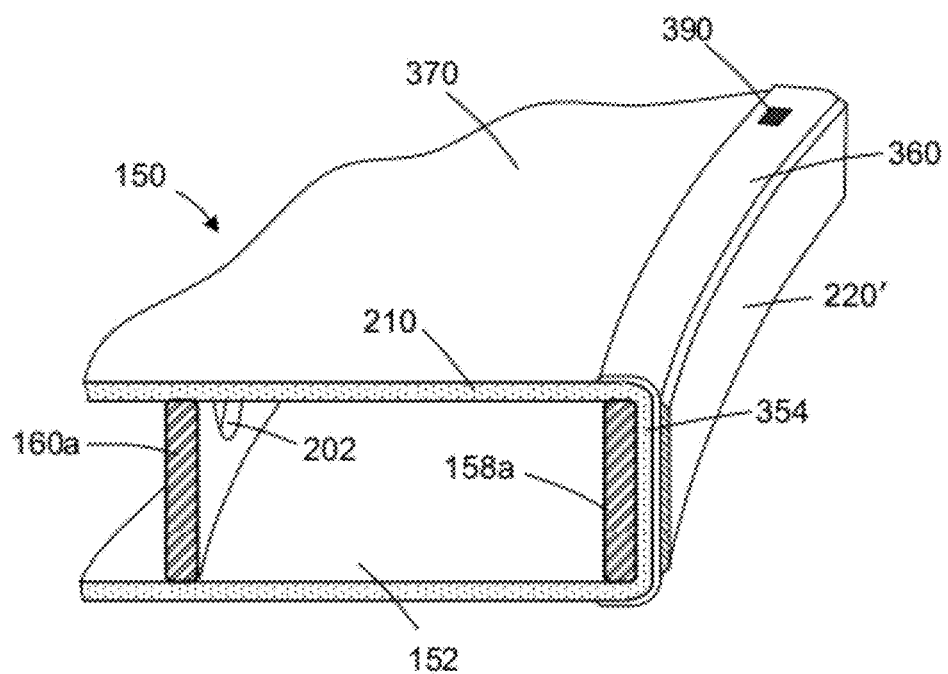
FIG. 10 is an enlarged cut-away view of a portion of the expanded thin-wall dielectric structure of FIG. 9 showing the electrode configuration.

Now turning to FIGS. 9 and 10, an alternate working end 122 with thin-wall dielectric structure 150 is shown. In this embodiment, the thin-wall dielectric structure 150 is similar to that of FIGS. 5 and 6 except that the second polarity electrode 220' that is exterior of the internal chamber 152 is disposed on a surface portion 370 of the thin-wall dielectric structure 150. In this embodiment, the second polarity electrode 220' comprises a thin-film conductive material, such as gold, that is bonded to the exterior of thin-wall material 210 along two lateral sides 354 of dielectric structure 150. It should be appreciated that the second polarity electrode can comprise one or more conductive elements disposed on the exterior of wall material 210, and can extend axially, or transversely to axis 111 and can be singular or multiple elements. In one embodiment shown in more detail in FIG. 10, the second polarity electrode 220' can be fixed on another lubricious layer 360, such as a polyimide film, for example KAPTON®. The polyimide tape extends about the lateral sides 354 of the dielectric structure 150 and provides protection to the wall 210 when it is advanced from or withdrawn into bore 120 in sleeve 110. In operation, the RF delivery method using the embodiment of FIGS. 9 and 10 is the same as described above, with RF current being capacitively coupled from the plasma 208 through the wall 210 and endometrial tissue to the second polarity electrode 220' to cause the ablation.

FIG. 9 further shows an optional temperature sensor 390, such as a thermocouple, carried at an exterior of the dielectric structure 150. In one method of use, the control unit 135 can acquire temperature feedback signals from at least one temperature sensor 390 to modulate or terminate RF energy delivery, or to modulate gas flows within the system. In a related method of the invention, the control unit 135 can acquire temperature feedback signals from temperature sensor 240 in interior chamber 152 (FIG. 6 to modulate or terminate RF energy delivery or to modulate gas flows within the system.

Figure 11:
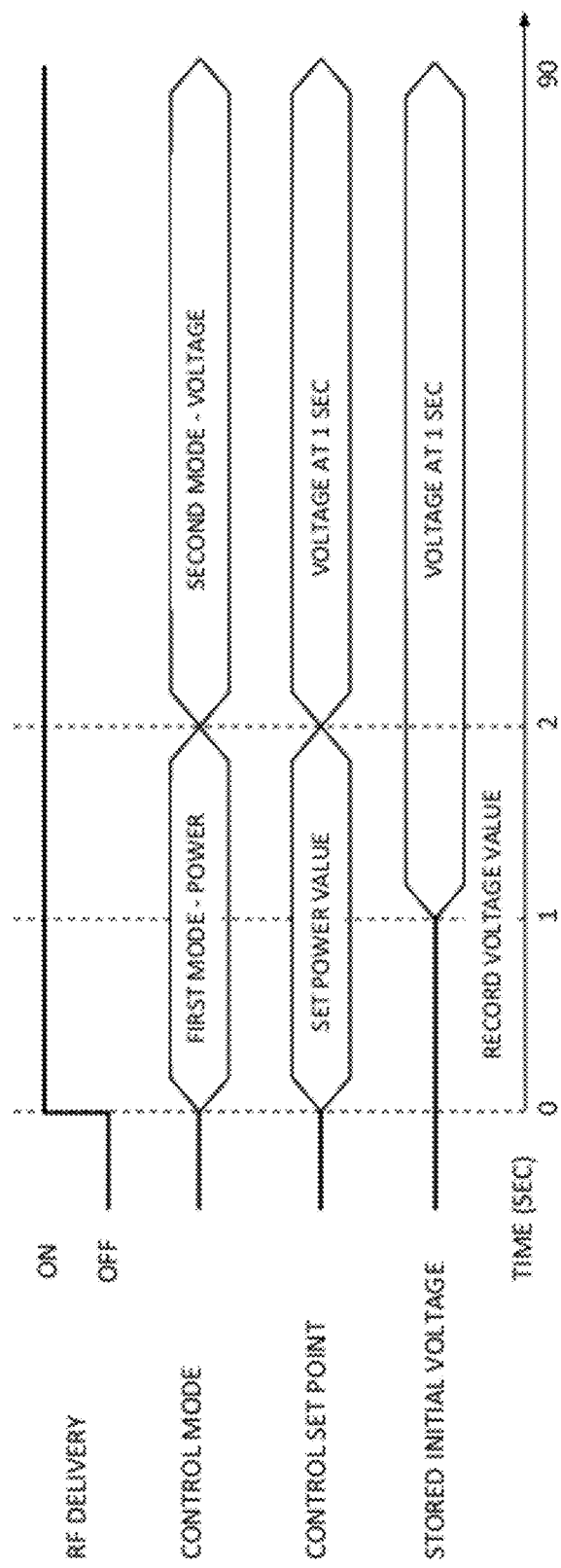
FIG. 11 is a diagram of a radiofrequency energy delivery apparatus and method corresponding to the invention.

In another aspect of the invention, FIG. 11 is a graphic representation of an algorithm utilized by the RF source 130A and RF controller 130B of the system to controllably apply RF energy in an endometrial ablation procedure. In using the expandable dielectric structure 150 of the invention to apply RF energy in an endometrial ablation procedure as described above, the system is configured to allow the dielectric structure 150 to open to different expanded dimensions depending on the size and shape of the uterine cavity 302. The axial length of dielectric structure 150 also can be adjusted to have a predetermined axial length extended outward from the introducer sleeve 110 to match a measured length of a uterine cavity. In any case, the actual surface area of the expanded dielectric structure 150 within different uterine cavities will differ—and it would be optimal to vary total applied energy to correspond to the differing size uterine cavities.

FIG. 11 represents a method of the invention that automatically determines relevant parameters of the tissue and the size of uterine cavity 302 to allow for selection of an energy delivery mode that is well suited to control the total applied energy in an ablation procedure. In embodiments, RF energy is applied at constant power for a first time increment, and the following electrical parameters (e.g., voltage, current, power, impedance) are measured during the application of energy during that first time increment. The measured electrical parameters are then used (principally, power and current, V=P/I) to determine a constant voltage to apply to the system for a second time interval. The initial impedance may be also be utilized by the controller as a shutoff criteria for the second treatment interval after a selected increase in impedance.

For example, in FIG. 11, it can be seen that a first step following the positioning of the dielectric structure in the uterine cavity 302 is to apply radiofrequency energy in a first mode of predetermined constant power, or constant RF energy ("FIRST MODE—POWER"). This first power is sufficient to capacitively couple current across the dielectric to contacted tissue, wherein empirical studies have shown the power can be in the range of 50 W-300 W, and in one embodiment is 80 W. This first power mode is applied for a predetermined interval which can be less than 15 seconds, 10 seconds, or 5 seconds, as examples, and is depicted in FIG. 11 as being 2 seconds. FIG. 11 shows that, in accordance with embodiments, the voltage value is determined a voltage sensor in controller 130A and is recorded at the "one-second" time point after the initiation of RF energy delivery. The controller includes a power sensor, voltage sensor and current sensor as is known in the art. This voltage value, or another electrical parameter, may be determined and recorded at any point during the interval, and more than one recording may be made, with averages taken for the multiple recordings, or the multiple recordings may be used in another way to consistently take a measurement of an electrical value or values. FIG. 11 next illustrates that the controller algorithm switches to a second mode ("SECOND MODE—VOLTAGE") of applying radiofrequency energy at a selected constant voltage, with the selected constant voltage related to the recorded voltage (or other electrical parameter) at the "one-second" time point. In one embodiment, the selected constant voltage is equal to the recorded voltage, but other algorithms can select a constant voltage that is greater or lesser than the recorded voltage but determined by a factor or algorithm applied to the recorded voltage. As further shown in FIG. 11, the algorithm then applies RF energy over a treatment interval to ablate endometrial tissue. During this period, the RF energy is varied as the measured voltage is kept constant. The treatment interval can have an automatic time-out after a predetermined interval of less that 360 seconds, 240 seconds, 180 seconds, 120 seconds or 90 seconds, as examples.

By using the initial delivery of RF energy through the dielectric structure 150 and contacted tissue in the first, initial constant power mode, a voltage level is recorded (e.g., in the example, at one second) that directly relates to a combination of (i) the surface area of the dielectric structure, and the degree to which wall portions of the dielectric structure have been elastically stretched; (ii) the flow rate of neutral gas through the dielectric structure and (iii) the impedance of the contacted tissue. By then selecting a constant voltage for the second, constant voltage mode that is directly related to the recorded voltage from the first time interval, the length of the second, treatment interval can be the same for all different dimension uterine cavities and will result in substantially the same ablation depth, since the constant voltage maintained during the second interval will result in power that drifts off to lower levels toward the end of the treatment interval as tissue impedance increases. As described above, the controller 130A also can use an impedance level or a selected increase in impedance to terminate the treatment interval.

The algorithm above provides a recorded voltage at set time point in the first mode of RF energy application, but another embodiment can utilize a recorded voltage parameter that can be an average voltage over a measuring interval or the like. Also, the constant voltage in the second mode of RF energy application can include any ramp-up or ramp-down in voltage based on the recorded voltage parameter.

In general, an electrosurgical method for endometrial ablation comprises positioning a RF ablation device in contact with endometrial tissue, applying radiofrequency energy in a first mode based on a predetermined constant power over a first interval, and applying radiofrequency energy in a second mode over a second interval to ablate endometrial tissue, the energy level of the second mode being based on treatment voltage parameters obtained or measured during the first interval. Power during the first interval is constant, and during the second period is varied to maintain voltage at a constant level. Another step in applying RF energy in the first mode includes the step of recording a voltage parameter in the first interval, wherein the voltage parameter is at least one of voltage at a point in time, average voltage over a time interval, and a change or rate of change of voltage. The second mode includes setting the treatment voltage parameters in relation to the voltage parameter recorded in the first interval.

Referring to FIG. 11, it can be understood that an electrosurgical system for endometrial ablation comprises a radiofrequency ablation device coupled to an radiofrequency power supply, and control means connected to the radiofrequency power supply for switching the application of radiofrequency energy between a constant power mode and a constant voltage mode. The control means includes an algorithm that (i) applies radiofrequency energy in the first mode (ii) records the voltage within a predetermined interval of the first mode, and (iii) applies radiofrequency energy in the second mode with constant voltage related to the recorded voltage.

In another aspect, the invention comprises a radiofrequency power supply, a means for coupling the radiofrequency power supply to an ablation device configured for positioning in a uterine cavity, the ablation device comprising a dielectric for contacting endometrial tissue, a system for recording an electrical parameter of the ablation device and contacted tissue, and a feedback system for varying the application of radiofrequency energy to tissue between a constant power mode and a constant voltage mode based on a recorded electrical parameter.

Figure 12:
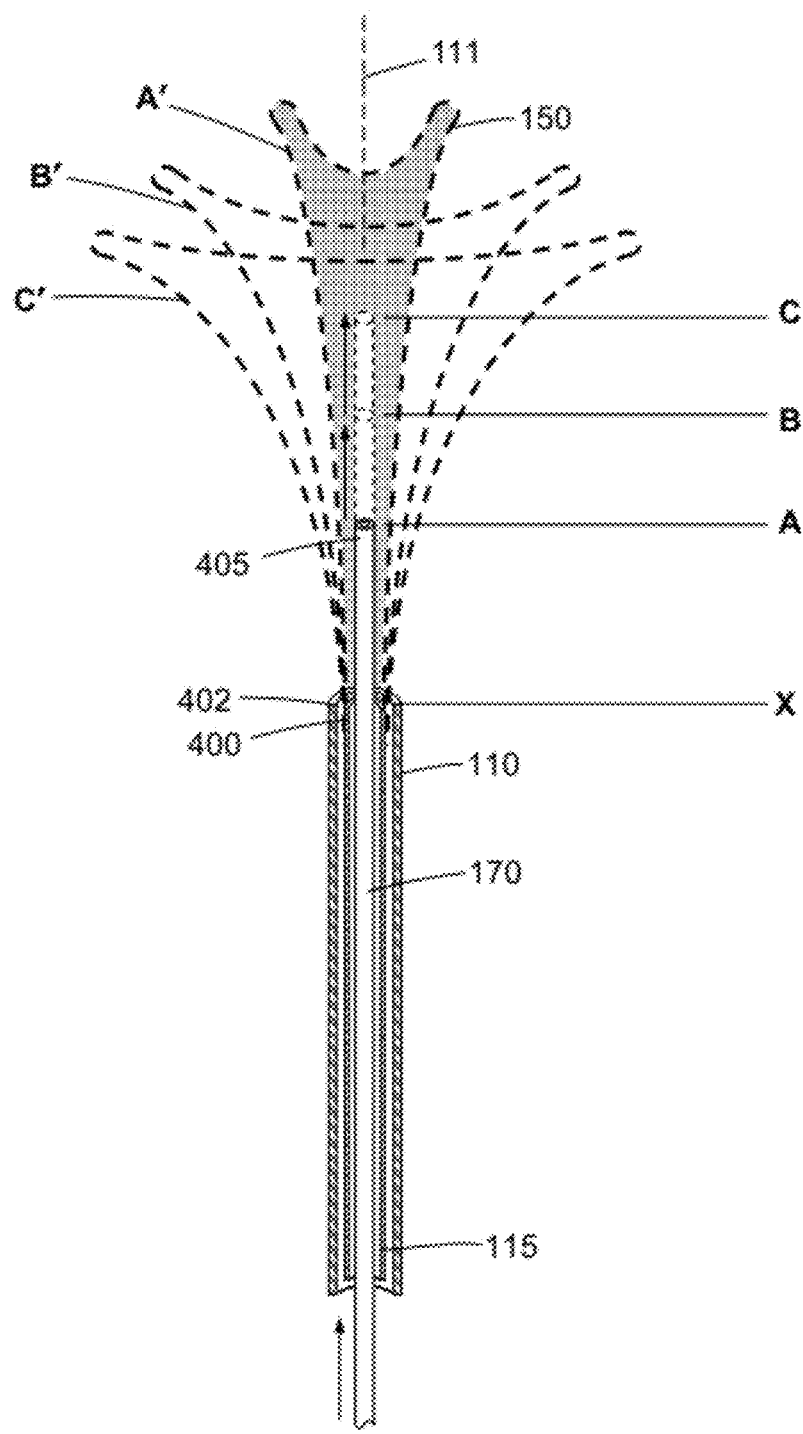
FIG. 12 is a schematic view of the working end of the ablation device of FIGS. 1-2 depicting three outlines of the expandable working end in a range of slightly-expanded to fully-expanded positions.
Figure 13:
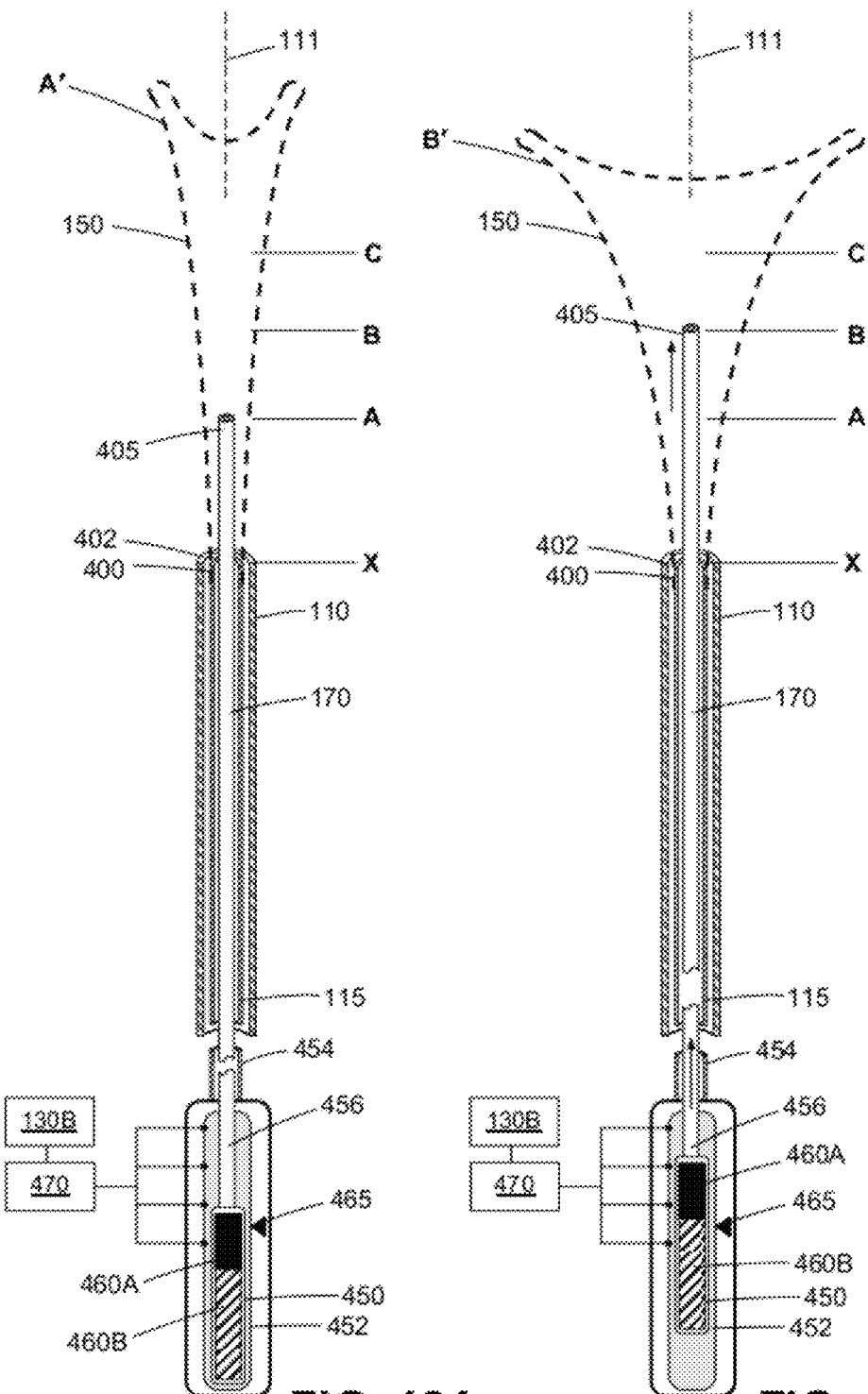
FIG. 13A is a schematic representation of an indicator mechanism in the handle of the ablation device of FIGS. 1-2 for indicating a first degree of expansion of the dielectric structure in a range shown in FIG. 12.
FIG. 13B is a schematic representation of the indicator mechanism of FIG. 13A indicating a second degree of expansion of the dielectric structure.

In another embodiment of the invention, FIGS. 12, 13A and 13B depict components of the ablation device of FIGS. 1-2 that provide the physician with an indication of the degree to which the dielectric structure 150 has opened in the patient's uterine cavity 302. It can be understood from FIGS. 5, 6 and 8C that the spring frame 155 that moves the dielectric structure 150 from a contracted, linear shape (FIG. 8B) to an expanded, triangular shape (FIG. 8C) results from actuating the handle 106 to move the assembly of inner sleeve 170, intermediate sleeve 115, frame 155 and dielectric structure 150 distally relative to the introducer sleeve 110 to thus expose and deploy the dielectric structure 150 in the uterine cavity 302.

Referring to FIG. 12, it can be seen that inner sleeve 170 and intermediate sleeve 115 are shown for convenience without their respective welded connections to spring frame elements 158*a*, 158*b*, 160*a* and 160*b*. The frame elements 158*a*, 158*b*, 160*a* and 160*b* and their springing function can be seen in FIGS. 5 and 6. In FIG. 12, the introducer sheath 110 is shown as being moved proximally relative to the dielectric structure 150 which corresponds to a position of the dielectric structure 150 shown in FIG. 8B. In the schematic view of FIG. 12, the distal end 400 of sleeve 170 has an axial position X and can be approximately the same axial position as the distal end 402 of the introducer sleeve 110. It can be understood that when the dielectric structure 150 and interior spring frame 155 are deployed in a uterine cavity, the spring force of frame 155 will tend to open the dielectric structure 150 from a position in FIG. 8B toward the position of FIG. 8C. In FIG. 12, an initial position of the distal end 405 of sleeve 170 has an axial position indicated at A which corresponds to plan shape A' of the dielectric structure 150. In a typical procedure, the spring force of frame 155 will move the distal end 405 of sleeve 170 toward an axial position B which corresponds to expanded dielectric plan shape B' or toward an axial position C and corresponding expanded dielectric plan shape C'. Dielectric plan C' represents a fully expanded dielectric structure 150. In order to allow the spring force of frame 155 to expand the frame and dielectric structure 150, the physician may gently and very slightly rotate, tilt and translate the expanding dielectric structure 150 in the uterine cavity 302. After thus deploying the dielectric structure, the different dimensions of uterine cavities will impinge on the degree of expansion of the dielectric structure 150—and the size and surface area of the dielectric structure, as an example, will be within the dimension range between plan shapes A' and plan shape C' of FIG. 12.

In one aspect of the invention, it is important for the system and physician to understand the degree to which the dielectric structure 150 and frame 155 has expanded in the uterine cavity. If the dielectric structure 155 has not expanded to a significant degree, it may indicate that the uterine cavity is very small or very narrow, that fibroids are impinging on dielectric structure preventing its expansion, that the uterine cavity is very asymmetric, or that a tip of the dielectric structure and frame 155 has penetrated into an endometrial layer, perforated the uterine wall or followed a dissection path created by a sounding procedure just prior to deployment of the dielectric structure. Further, in one system embodiment, the dielectric structure 150 is preferred to have a minimum surface area directly related to its expanded shape to thus cooperate with an RF energy delivery algorithm.

In one embodiment, the system provides a "degree of frame-open" signaling mechanism for signaling the physician that the frame 155 and dielectric structure 150 has expanded to a minimum predetermined configuration. The signaling mechanism is based on the relative axial location of inner sleeve 170 and sleeve 115 as can be understood from FIGS. 12 and 13A-13B. In FIGS. 1 and 2, it can be seen that a sliding element 450 is exposed in a top portion of handle component 114B to slide axially in a slot 452. In a schematic view of handle component 114b in FIGS. 13A-13B, it can be seen that the proximal end 454 of sleeve 115 is fixed in handle component 114b. Further, the proximal end of 456 of the inner sleeve 170 is connected to the sliding element 450 that slides in slot 452. Thus, it can be understood that inner sleeve 170 is slidable and free-floating in the bore 175 of sleeve 115 and can be moved axially to and fro depending to the opening spring force of frame 155—which force can be constrained by the frame being withdrawn into the bore 120 of introducer sleeve 110 or by uterine walls impinging on the dielectric structure 150 and frame 155 when deployed in a uterine cavity. As can be seen in FIGS. 1, 2, 13A and 13B, the sliding element has at least two axially-extending indicators 460A and 460B that can be different colors that slide axially relative to status-indicating arrow element 465 in a fixed location in the handle 114b. In one embodiment, indicator 460A can be red for "stop" and indicator 460B can be "green", for indicating whether to stop proceeding with the procedure, or to go ahead with the ablation procedure. In FIG. 13A, it can be seen that inner sleeve 170 and its distal end 405 are only axially extended at point A which corresponds to dielectric expansion profile A'. The limited expansion of dielectric structure at profile A' is indicated at the slider 450 wherein the arrow 465 points to the red 'stop" indicator 460A which indicates to the physician to stop and not proceed with the ablation procedure due to limited expansion of dielectric structure 150.

FIG. 13B depicts an extension of inner sleeve 170 and its distal end 405 to axially extended at point B which corresponds to dielectric expansion profile B'. This intermediate expansion of dielectric structure 150 at profile B' is indicated to the physician by observing slider 450 wherein arrow 465 points to the green indicator 460B which indicates "go"—that is, the physician can proceed with the ablation procedure since the dielectric structure 150 and frame 155 have expanded to a predetermined degree that cooperates with an RF energy delivery algorithm. It can be understood from FIG. 13B that sleeve 170 can move axially toward extended position C with corresponding dielectric structure profile C' and indicator arrow 465 will again point to the "go" portion 460B of sliding element which is green.

In another aspect of the invention also depicted in FIGS. 13A-13B, the handle component 114b can include a electrical contact sensor 470 that detects the axial movement of sliding element 450 and sleeve 170 relative to sleeve 115 to thereby provide an electronic signal indicating the degree of expansion of the frame 155 and dielectric structure 150. In one embodiment, the electronic signal communicates with RF controller 130B to disable the system if the relative axial positions of sleeves 170 and 115 do not indicate a predetermined degree of expansion of the frame 155 and dielectric structure. The system can further include an override mechanism, whereby the physician can manipulate the instrument slightly back and forth and rotationally to evaluate whether the frame 155 opens incrementally more. In another embodiment, the electrical sensor 470 can detect a plurality of degrees of expansion of the frame 155 and dielectric structure 150, for example as depicted by an electrical contact be activated at positions AA, BB, CC, and DD of the slider 450 in FIGS. 13A-13B, wherein each degree of expansion of frame 155 signals the controller to select a different RF delivery algorithm. The various different RF delivery algorithms can alter at least one of: (i) the duration of a treatment interval, for example from between 60 seconds and 240 seconds, (ii) the relation between a recorded voltage and a treatment voltage as described in the text accompanying FIG. 11 above (e.g., the treatment voltage can equal the recorded voltage, or vary as a factor about 0.8, 0.9, 1.0, 1.1 or 1.2 times the recorded voltage; (iv) can vary a ramp-up or ramp-down in voltage, or can a time interval of the first and second modes of RF energy delivery described above. The number of degrees of expansion of frame 155 and dielectric structure can range from 1 to 10 or more.

The embodiment of FIGS. 1, 2, 13A and 13B depict indicator subsystems that include visual and electrical signals, but it should be appreciated that the indicator subsystem can provide any single or combination signals that can be visual, aural or tactile with respect to the operator and/or electrically communicate with microprocessors, programmable logic devices or controllers of the ablation system.

Figure 14:
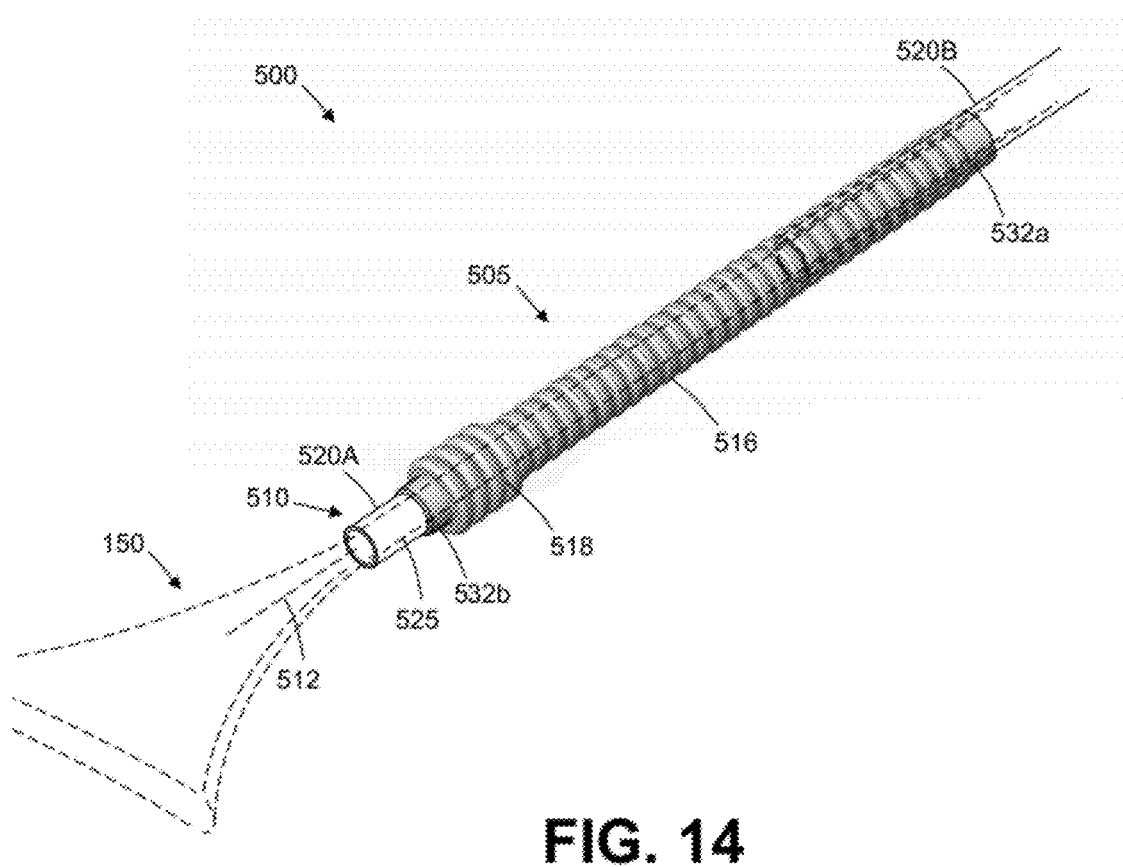
FIG. 14 is a perspective view of an alternative working end of an endometrial ablation system with an elongated, elastomeric bellows-like seal for sealing the patient's cervical canal.

In another embodiment of the invention, FIGS. 14-16B illustrate another system embodiment 500 that is similar to previous embodiments except that another cervical sealing structure or element is shown. FIG. 14 shows a cervical seal 505 carried by a distal portion of the introducer sleeve assembly 510 that extends along longitudinal axis 512. The elongated cervical seal 505 comprises a flexible material with an annular thin wall 515 formed with a plurality of annular ridges or undulations 516 spaced apart by annular recesses 518. The annular ridges provide a bellows-like form. The seal 505 can be fabricated of a biocompatible elastomeric material such as silicone. The elastomeric material also can have reinforcing braids or woven material therein, or can have metal spring wire material therein. The sleeve assembly 510 comprises concentric polymer or metal sleeves as shown in FIG. 14, 15A-15B including first outer sleeve 520A and inner sleeve 520B. A bore or passageway 525 in the inner sleeve 520B is configured for carrying and deploying an ablating dielectric structure 150 as depicted in FIG. 9. The elongated cervical seal 505 has proximal end 530a and distal end 530b. In FIGS. 14 and 15A-15B, it can be seen that proximal end 530a of seal 505 is bonded to a distal region 532a of outer sleeve 520A and distal end 530b of seal 505 is bonded to a distal region 532b of inner sleeve 520B. The sealing element or seal 505 is coupled to the sleeves 520A and 520B by bonds indicated at 536 which can comprise any suitable adhesive, glue, ultrasonic bonding or the like.

In FIGS. 15A-15B, it can be understood that axial movement of sleeve 520B relative to sleeve 520A can axially compress or axially extend the seal 505. In one embodiment, the seal 505 is a molded material having a repose form shown in FIG. 15A with a plurality of annular ridges 516 and annular recesses 518 with the height AA of the ridges ranging from about 1 mm to 6 mm around the sleeve assembly 510 which has an outer diameter ranging from about 3 mm to 8 mm. The annular ridges 516 can have a width of 0.5 to 5 mm and similarly the annular recesses 518 can have a width of 0.5 to 5 mm. The annular ridges and recesses can have similar or dissimilar widths, and such widths can vary over the axial length of the seal. The thickness of the thin wall material can range from 0.001" to 0.1". The length BB of the seal 505 (FIG. 15A) in its repose state can be at least 2 cm, 4 cm or 6 cm. A finger grip 540 is coupled to a proximal end 542 of the outer sleeve 520A that can be used to move the outer sleeve 520A relative to the inner sleeve 520B.

In one embodiment, still referring to FIGS. 14 and 15A, it has been found useful that the distal region of seal 505 has ridges 516 having a greater height AA for engaging and sealing around the internal cervical os 320 and a lesser height of ridges 516 for the seal portion that extends through the cervical canal. In the embodiment of seal 505 shown in FIGS. 14 and 15A, the exterior profile of the seal's repose state has a distal portion 544a with a first outermost diameter and a proximal portion with a second lesser diameter, but it should be appreciated that the external profile of the seal 505 can be tapered in the proximal direction or can have a plurality of tapers along the overall length BB of the seal.

In a method of use, it has been found that an elongate seal 505 with a plurality of annular ridges 516 of an elastomeric material inserted into a cervical canal creates an effective seal since the ridges can deform independently to accommodate any shape and dimension of cervical canal. In FIG. 15A, it can be understood that the seal 505 is molded having length B, but can be axially compressed to a shorter axial length for sealing a cervical canal. For insertion into a cervical canal, the seal 505 can be axially stretched as shown in FIG. 15B to have an outside diameter similar to the diameter of the sleeve assembly 510. FIG. 15B shows that the seal 505 when axially stretched has the annular regions 516 and 518 pre-disposed to fold or deploy into the ridges, but it should be appreciated that the seal 505 can be stretched so that the seal is without undulations until the stretched seal is tight against the outer sleeve 520A. The sleeve assembly 510 can have a lock and release mechanism in grip 540 to lock the seal 505 in an extended position in preparation of insertion into a patient's cervical canal. In the embodiment of FIG. 15A, it can be seen that grip 540 has a button mechanism 545 that can press against inner sleeve 520B to lock the sleeves in a selected axial relationship. The lock and release mechanism can have an element that engages the inner sleeve 520B or can deform the outer sleeve 520A to prevent its slippage relative to the inner sleeve.

Figure 16A:
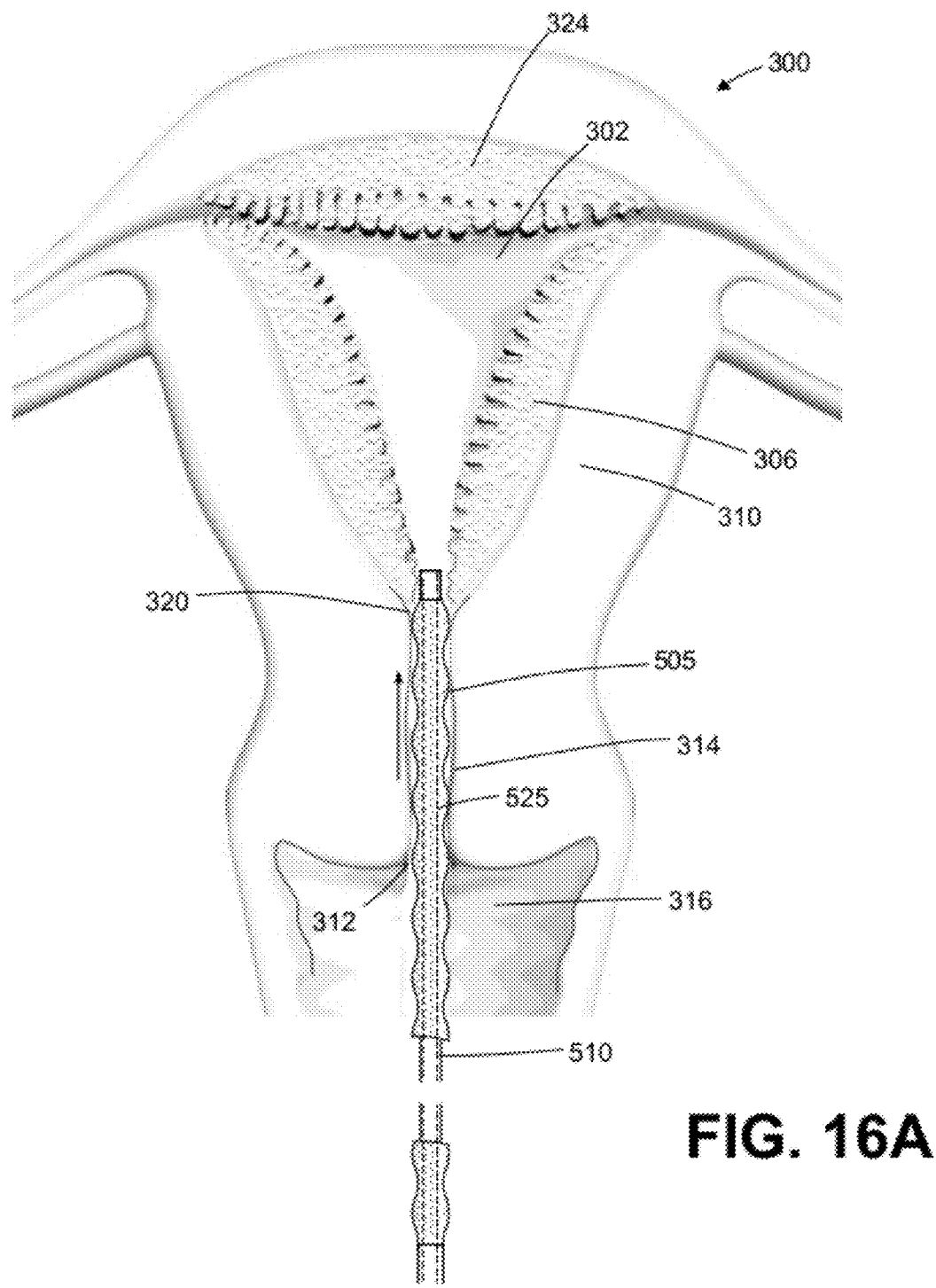
FIG. 16A is a schematic view of a method of the invention illustrating the step introducing an introducer sleeve with the seal of FIG. 14 into a patient's uterus.
Figure 16B:
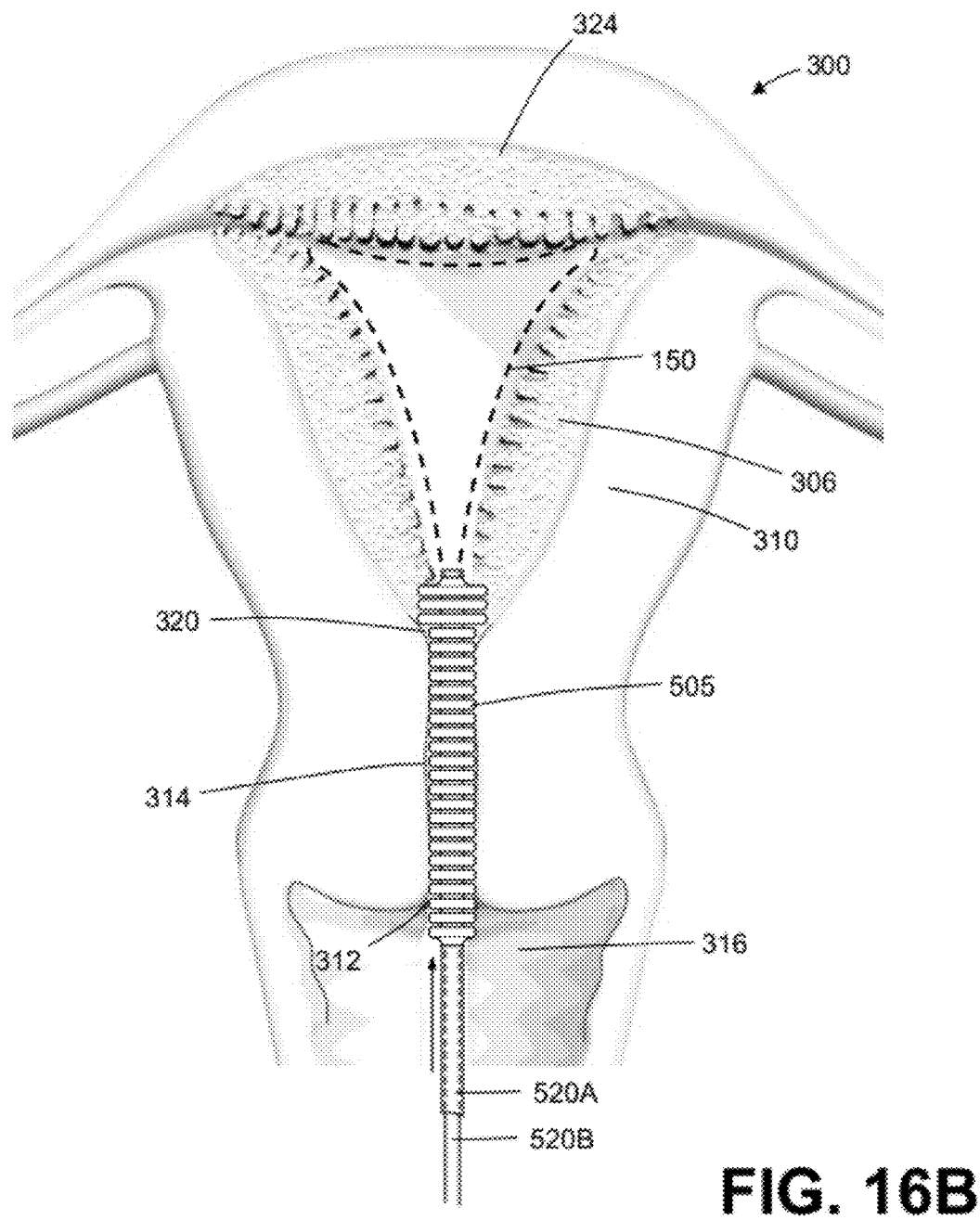
FIG. 16B is a schematic view of a subsequent step of deploying the seal of FIG. 14 in the patient's cervical canal.

FIGS. 16A and 16B illustrate a method of using the system embodiment 500 of FIG. 14 in accessing a patient's uterine cavity 302 and sealing the cervical canal 314, which is useful for performing a uterine cavity integrity check and for prevented heated fluids from migrating into the cervical canal during an endometrial ablation procedure. FIG. 16A illustrates a first step of the method in which the elastomeric seal 505 is axially extended or stretched by moving the sleeve assembly as shown in FIG. 15B, and thereafter the assembly is inserted into the cervical canal. It should be appreciated that the seal 505 and sleeve assembly also can be inserted into the cervical canal without stretching the seal, and the step of pushing the assembly distally through the outer cervical os 312 would cause the seal to stretch and allow it passage through the cervical canal. FIG. 16B illustrates a subsequent step of the method wherein the physician actuates the outer sleeve 520A moving it distally relative to inner sleeve 520B to axially compress the seal which results in the seal assuming the expanded cross-section form with corrugated surfaces wherein the ridges 516 contact tissue about the cervical canal 314.

Still referring to FIG. 16B, the physician can introduce an ablating dielectric structure 150 through passageway 525 in the sleeve assembly and open the frame of the ablation working end 122 (phantom) view, either before or after the seal 505 is deployed and expanded in the cervical canal. After the seal 505 is deployed as shown in FIG. 16B, the uterine cavity can be characterized as non-perforated or perforated as described above, and the ablation system can be actuated as described above. Upon completion of an endometrial ablation procedure, the seal 505 can be moved the position of FIG. 16A, the dilectric structure 150 is collapsed and withdrawn into passageway 525 and the sleeve assembly 510 and dielctric structure 150 can be withdrawn from the patient's cervical canal.

Figure 17:
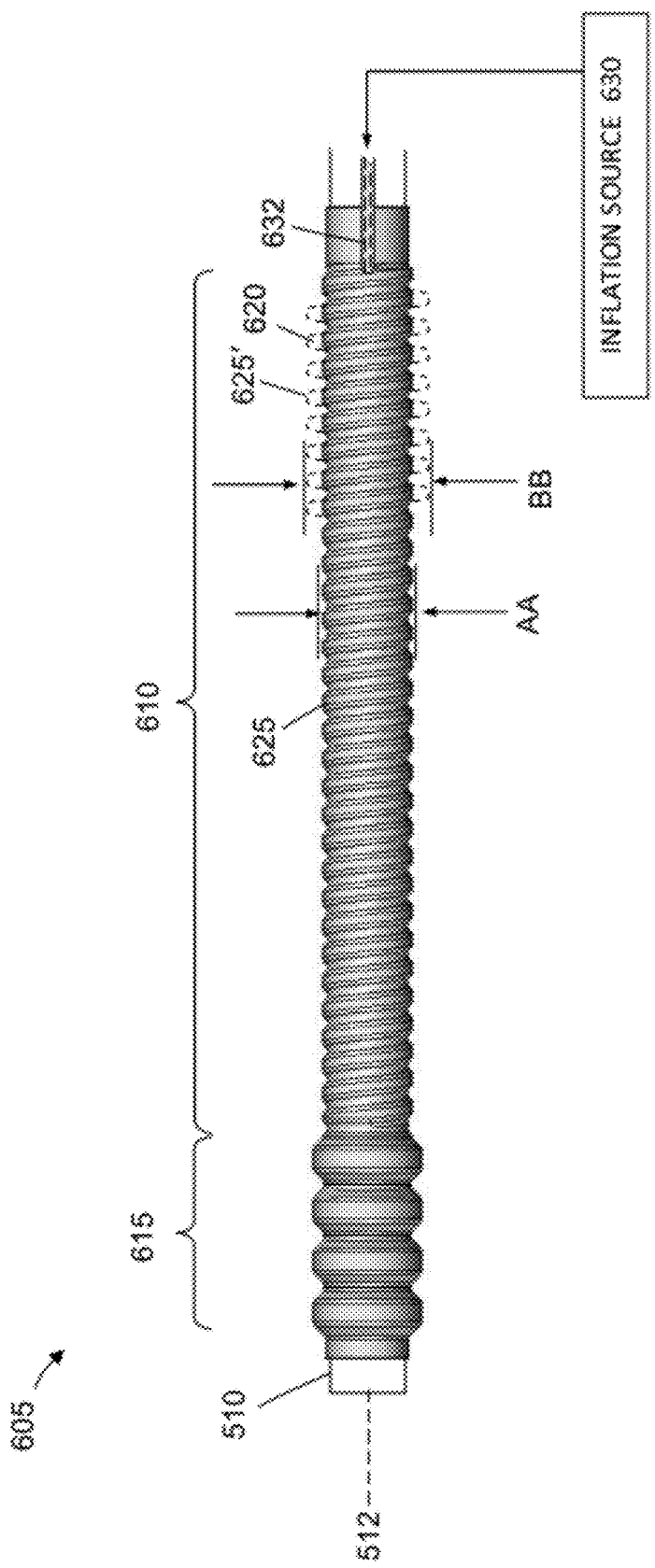
FIG. 17 is a side view of another embodiment of an elongated, elastomeric bellows-like seal for sealing the patient's cervical canal.

FIG. 17 illustrates another embodiment of cervical sealing structure 605 or seal which is similar to previous embodiments. The seal 605 of FIG. 17 again is carried by a distal portion of the introducer sleeve assembly 510 that extends along longitudinal axis 512. The elongated cervical seal 605 comprises a thin wall silicone or similar elastomeric with an elongated helical ridge region 610. The seal 605 is configured for axial deformation as described in the previous embodiment between a first transversely expanded shape for engaging a cervical canal and a second transversely non-expanded shape for trans-cervical insertion. In FIG. 17, the seal is depicted in its repose shape and can be stretched to reduce its transverse section for introducing into a cervical canal. The seal 605 of FIG. 17 has a distal region 615 of annular ribs 618 as described in the previous embodiment, but such ribs 618 also could have a helical configuration.

Figure 18:
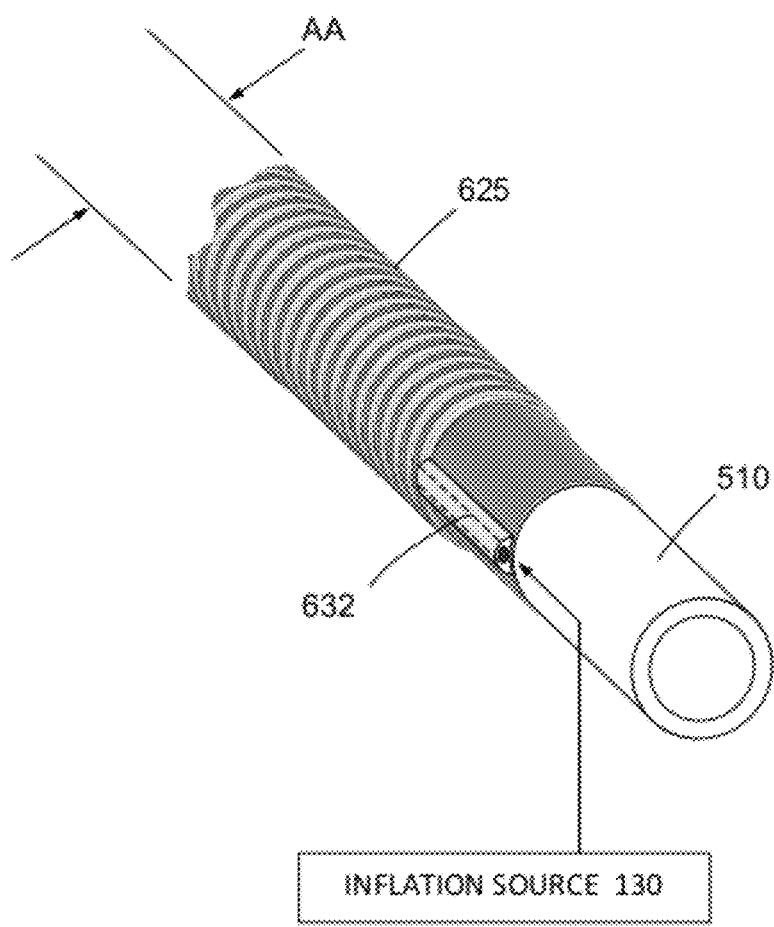
FIG. 18 is a side view of another embodiment of an elongated, elastomeric bellows-like seal for sealing the patient's cervical canal.

FIGS. 17-18 further show that an interior chamber 620 at the interior thin wall material 622 which can expand or inflate the helical ridge 625 when pressurized with fluid that is in communication with an inflation source 630. The inflation fluid can be provided by any gas or liquid source, such as a syringe filled with air, $CO_2$ or another biocompatible gas. In one embodiment, the inflation source 630 is fluidly coupled to a lumen 632 in the wall of seal as shown in FIGS. 17-18. Thus, the seal 605 can be configured with a first maximum expanded transverse dimension AA (FIGS. 17-18) by the relative axial position of the sleeves as described above. Further, the seal 605 can be configured with at least a second greater expanded transverse dimension BB (FIGS. 17-18) which results from pressurizing the interior chamber 620 which effectively stretches or bulges the helical ridges 625 to an expanded shape 625'.

Figure 19:
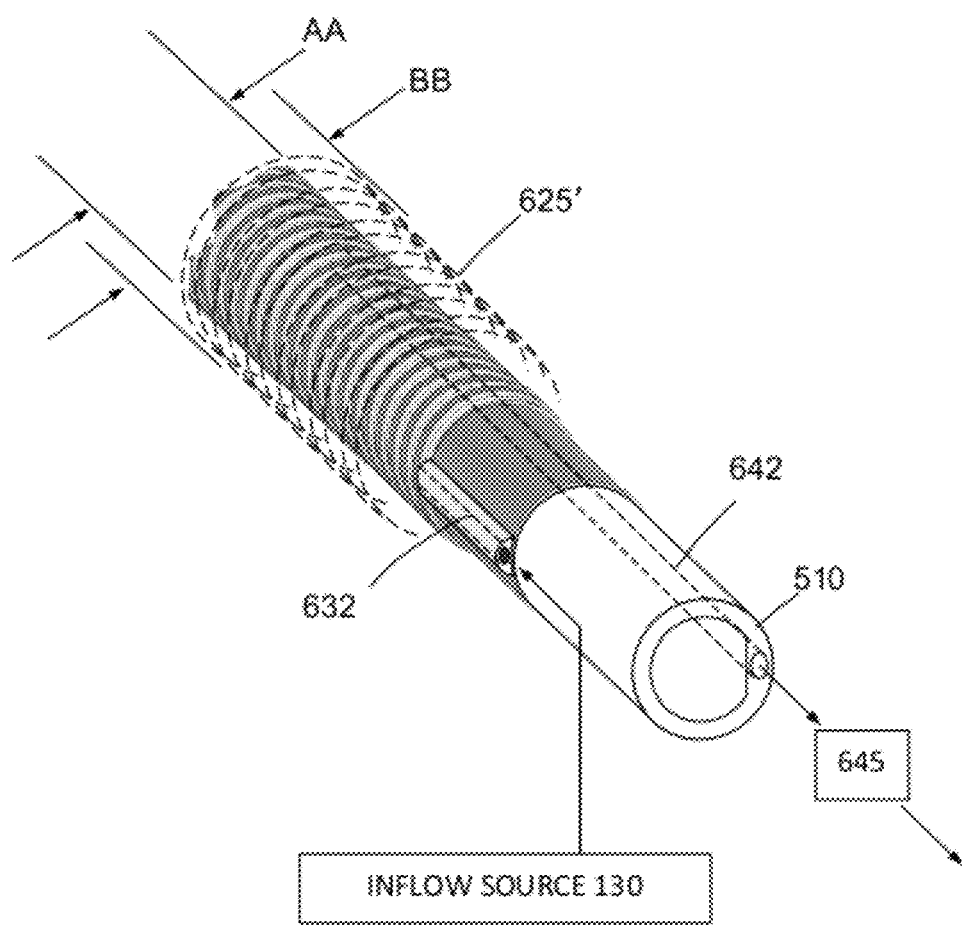
FIG. 19 is a side view of another embodiment of an elongated, elastomeric bellows-like seal for sealing the patient's cervical canal.

FIG. 19 illustrates another embodiment which functions similar to that of FIG. 17, except that a fluid inflow source 640 is coupled to lumen 632 to provide a continuous flow of gas or liquid through the interior chamber which can exit another lumen 642 in sleeve assembly 510. The inflow source 640 can pressurize and expand the ridges 625 of the seal and a restrictor valve 645 can control outflows to thus expand the seal and provide a fluid flow through the seal 605 for cooling the seal assembly.

Figure 20:
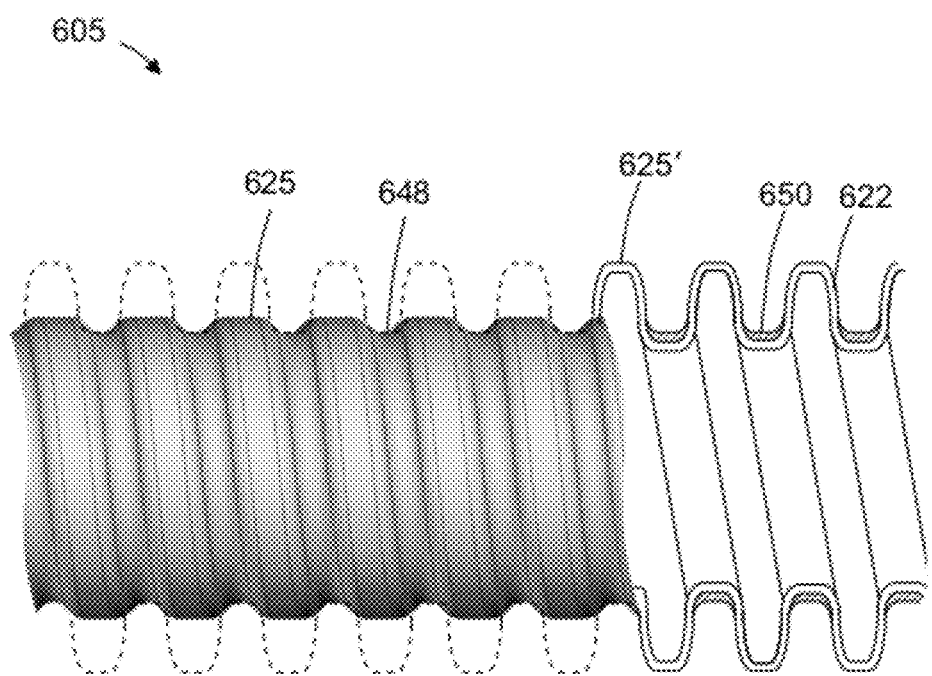
FIG. 20 is a side view of another embodiment of an elongated, elastomeric bellows-like seal for sealing the patient's cervical canal.

FIG. 20 shows another embodiment in cut-away view wherein the seal 605' includes means for causing the ridges 625 to expand while the valleys 648 of the seal are resistant to radial expansion. In one embodiment, the helical valley 648 is over molded with a higher durometer material 650 that allows for axial compression of the seal but resists radial inflation. In another embodiment, the helical valley 648 can be configured with a much thicker elastomer than the ridges 625, to prevent radial expansion of the valleys. In another embodiment, the helical valley 648 can include an embedded helical spring element.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system for treating uterine tissue, comprising:
   an introducer member having first and second concentric sleeves and being configured for trans-cervical insertion to access a uterine cavity of a patient, said introducer member having a central lumen;
   a deformable thin-wall seal carried by the introducer, wherein proximal and distal ends of the seal are fixedly attached to the first and second concentric sleeves, respectively, so that relative axial movement of the sleeves causes the seal to transition between a first transversely expanded shape having a first transverse dimension for engaging a cervical canal and a second transversely non-expanded shape for trans-cervical insertion, wherein the seal may be stretched tight against the introducer member by distally extending the second concentric sleeve relative to the first concentric sleeve; and
   a fluid source in communication with an interior region of the seal for transverse expansion of the seal, wherein the interior region of the seal may be inflated to an expanded transverse dimension greater than the first transverse dimension which resulted from movement of the sleeves.

2. The system of claim 1, wherein the seal comprises an elastomeric material.

3. The system of claim 1, wherein the seal comprises a thin wall silicone.

4. The system of claim 1, wherein the seal is formed with helical ridge and valley regions for folding and unfolding upon said axial deformation.

5. The system of claim 1, wherein the introducer member comprises a first lumen to provide a continuous flow of gas or liquid through an interior chamber of the deformable thin-wall seal and a second lumen to provide a restricted outflow of fluid from the interior chamber to expand the seal and provide a fluid flow for cooling the seal.

6. The system of claim 5, further comprising a restrictor valve in the second lumen.

* * * * *